US005985309A

United States Patent [19]

Edwards et al.

[11] Patent Number: 5,985,309

[45] Date of Patent: Nov. 16, 1999

[54] PREPARATION OF PARTICLES FOR INHALATION

[75] Inventors: David A. Edwards, State College, Pa.; Robert S. Langer, Newton; Rita Vanbever, Cambridge, both of Mass.; Jeffrey Mintzes, State College, Pa.; Jue Wang, State College, Pa.; Donghao Chen, State College, Pa.

[73] Assignee: Massachusetts Institute of Technology, Cambridge, Mass.

[21] Appl. No.: 08/971,791

[22] Filed: Nov. 17, 1997

Related U.S. Application Data

[63] Continuation of application No. 08/784,421, Jan. 16, 1997

[60] Provisional application No. 60/059,004, Sep. 19, 1997.

[51] Int. Cl.$^6$ .......... A61K 13/00

[52] U.S. Cl. .......... 424/426; 424/434; 424/489; 424/501

[58] Field of Search .......... 424/434, 489, 424/426, 490, 491–500, 501–502, 43, 45, 46

[56] References Cited

U.S. PATENT DOCUMENTS

| | | | |
|---|---|---|---|
| 2,470,296 | 5/1949 | Fields | 427/213.31 |
| 2,533,065 | 3/1950 | Taplin et al. | 424/497 |
| 2,992,645 | 7/1961 | Fowler | 128/203.21 |

(List continued on next page.)

FOREIGN PATENT DOCUMENTS

| | | |
|---|---|---|
| 0 072 048 | 2/1983 | European Pat. Off. . |
| 0 213 303 | 6/1986 | European Pat. Off. . |
| 0 257 915 | 3/1988 | European Pat. Off. . |
| 0 324 938 | 7/1989 | European Pat. Off. . |
| 0 335 133 | 10/1989 | European Pat. Off. . |
| 0 458 745 | 5/1991 | European Pat. Off. . |
| 1 288 583 | 11/1969 | United Kingdom . |

(List continued on next page.)

OTHER PUBLICATIONS

Sela et al., "Multichain Polyamino Acids," *J. Am. Chem. Soc.,* 78:746 (1956).

Smith, et al. "Aerosol Administration of Antibiotics" *Respiration,* 62(1) 19–24 (1995).

Smith, "Peptide delivery via the pulmonary route: a valid approach for local and systemic delivery" *J. Contr. Rel.* 46: 99–106 (1997).

(List continued on next page.)

*Primary Examiner*—S. Mark Clardy
*Assistant Examiner*—Kathryne E. Shelborne
*Attorney, Agent, or Firm*—Hamilton, Brook, Smith & Reynolds, P.C.

[57] ABSTRACT

Particles incorporating a surfactant and/or a hydrophilic or hydrophobic complex of a positively or negatively charged therapeutic agent and a charged molecule of opposite charge for drug delivery to the pulmonary system, and methods for their synthesis and administration are provided. In a preferred embodiment, the particles are made of a biodegradable material and have a tap density less than 0.4 g/cm$^3$ and a mass mean diameter between 5 $\mu$m and 30 $\mu$m, which together yield an aerodynamic diameter of the particles of between approximately one and three microns. The particles may be formed of biodegradable materials such as biodegradable polymers. For example, the particles may be formed of poly(lactic acid) or poly(glycolic acid) or copolymers thereof. Alternatively, the particles may be formed solely of a therapeutic or diagnostic agent and a surfactant. Surfactants can be incorporated on the particle surface for example by coating the particle after particle formation, or by incorporating the surfactant in the material forming the particle prior to formation of the particle. Exemplary surfactants include phosphoglycerides such as dipalmitoyl phosphatidylcholine (DPPC). The particles can be effectively aerosolized for administration to the respiratory tract to permit systemic or local delivery of wide a variety of therapeutic agents. Formation of complexes of positively or negatively charged therapeutic agents with molecules of opposite charge can allow control of the release rate of the agents into the blood stream following administration.

27 Claims, 4 Drawing Sheets

U.S. PATENT DOCUMENTS

| | | | |
|---|---|---|---|
| 3,781,230 | 12/1973 | Vassiliades et al. | 206/387.1 |
| 3,957,965 | 5/1976 | Hartley et al. | 424/452 |
| 4,009,280 | 2/1977 | Macarthur et al. | 514/456 |
| 4,089,800 | 5/1978 | Temple | 427/213.31 |
| 4,161,516 | 7/1979 | Bell | 424/451 |
| 4,173,488 | 11/1979 | Vassiliades et al. | 106/216.1 |
| 4,272,398 | 6/1981 | Jaffe | 427/213.31 |
| 4,352,883 | 10/1982 | Lim | 435/178 |
| 4,391,909 | 7/1983 | Lim | 435/1.1 |
| 4,466,442 | 8/1984 | Hilmann et al. | 600/431 |
| 4,524,769 | 6/1985 | Wetterlin | 128/203.15 |
| 4,572,203 | 2/1986 | Feinstein | 424/9.52 |
| 4,590,206 | 5/1986 | Forrester et al. | 514/456 |
| 4,615,697 | 10/1986 | Robinson | 424/428 |
| 4,679,555 | 7/1987 | Sackner | 128/203.15 |
| 4,741,872 | 5/1988 | De Luca et al. | 264/4.7 |
| 4,743,545 | 5/1988 | Torobin | 435/41 |
| 4,774,958 | 10/1988 | Feinstein | 424/9.52 |
| 4,789,550 | 12/1988 | Hommel et al. | 424/493 |
| 4,818,542 | 4/1989 | DeLuca et al. | 424/491 |
| 4,847,091 | 7/1989 | Illum | 424/455 |
| 4,855,144 | 8/1989 | Leong et al. | 514/772.3 |
| 4,857,311 | 8/1989 | Domb et al. | 427/213.31 |
| 4,861,627 | 8/1989 | Mathiowitz et al. | 264/122 |
| 4,865,789 | 9/1989 | Castro et al. | 424/490 |
| 4,904,479 | 2/1990 | Illum | 424/490 |
| 4,917,119 | 4/1990 | Potter et al. | 424/491 |
| 4,976,968 | 12/1990 | Steiner | 424/497 |
| 4,994,281 | 2/1991 | Muranishi et al. | 128/203.21 |
| 5,033,463 | 7/1991 | Cocozza | 206/387.1 |
| 5,064,065 | 11/1991 | Lew | 427/213.33 |
| 5,069,936 | 12/1991 | Yen | 427/213.33 |
| 5,075,109 | 12/1991 | Tice et al. | 424/426 |
| 5,100,669 | 3/1992 | Hyon et al. | 600/431 |
| 5,123,414 | 6/1992 | Unger | 424/487 |
| 5,160,745 | 11/1992 | DeLuca et al. | 521/64 |
| 5,169,871 | 12/1992 | Hughes et al. | 600/438 |
| 5,195,520 | 3/1993 | Schlief et al. | 424/434 |
| 5,204,108 | 4/1993 | Illum | 424/454 |
| 5,204,113 | 4/1993 | Hartley et al. | 514/291 |
| 5,260,306 | 11/1993 | Boardman et al. | 427/213.31 |
| 5,271,961 | 12/1993 | Mathiowitz et al. | 128/203.12 |
| 5,327,883 | 7/1994 | Williams et al. | 424/9.51 |
| 5,334,381 | 8/1994 | Unger | 424/9.51 |
| 5,352,435 | 10/1994 | Unger | 424/9.51 |
| 5,384,133 | 1/1995 | Boyes et al. | 341/22 |
| 5,393,524 | 2/1995 | Quay | 424/9.52 |
| 5,407,609 | 4/1995 | Tice et al. | 264/4.6 |
| 5,456,917 | 10/1995 | Wise et al. | 424/426 |
| 5,478,578 | 12/1995 | Arnold et al. | 424/499 |
| 5,482,946 | 1/1996 | Clark et al. | 514/291 |
| 5,518,709 | 5/1996 | Sutton et al. | 424/9.52 |
| 5,607,695 | 3/1997 | Ek et al. | 424/468 |
| 5,612,053 | 3/1997 | Baichwal | 424/440 |

FOREIGN PATENT DOCUMENTS

| | | |
|---|---|---|
| WO 80/02365 | 11/1980 | WIPO . |
| WO 88/04556 | 6/1988 | WIPO . |
| WO 88/09163 | 12/1988 | WIPO . |
| WO 91/04732 | 4/1991 | WIPO . |
| WO 91/0627 | 5/1991 | WIPO . |
| WO 91/06286 | 5/1991 | WIPO . |
| WO 91/12823 | 9/1991 | WIPO . |
| WO 92/18164 | 10/1992 | WIPO . |
| WO 92/21382 | 12/1992 | WIPO . |
| WO 93/25221 | 12/1993 | WIPO . |
| WO 94/07514 | 4/1994 | WIPO . |
| WO 94/08627 | 4/1994 | WIPO . |
| WO 94/16739 | 4/1994 | WIPO . |
| WO 95/00127 | 1/1995 | WIPO . |
| WO 95/07072 | 3/1995 | WIPO . |
| WO 95/24183 | 9/1995 | WIPO . |
| WO 96/09814 | 4/1996 | WIPO . |
| WO 96/15814 | 5/1996 | WIPO . |
| WO 97/36574 | 10/1997 | WIPO . |

OTHER PUBLICATIONS

Strand, et al. "Radiolabeled Colloids and Macromolecules in the Lymphatic System" Critical *Reviews in Therapeutic Drug Carrier Systems* 6(3): 211–238 (1989).

Swift, "The oral airway—a conduit or collector for pharmaceutical aerosols?" Respiratory Drug Delivery IV, 187–194 (1994).

Tabata et al., "Controlled Delivery Systems for Proteins Using Polyanhydride Microspheres," *Pharm. Res.,* 10(4): 487–496 (1993).

Tabata and Ikada, "Effect of surface wettability of microspheres on phagocytosis," *J. Colloid and Interface Sci.,* 127(1): 132–140 (1989).

Tabata and Ikada, "Macrophage Phagocytosis of Biodegradable Microspheres Composed of L–lactic Acid/Glycolic Acid Homo– and Copolymers," *J. Biomed. Mater. Res.,* 22: 837–858 (1988).

Tabata and Ikada, "Effect of size and surface charge of polymer microspheres on their phagocytosis by macrophage," *J. Biomed. Mater. Res.,* 22:837 (1988).

Taburet, et al. "Pharmacokinetic Optimisation of Asthma Treatment" *Clin. Pharmacokinet.* 26(5): 396–418 (1994).

* Tansey, "The challenges in the development of metered dose inhalation aerosols using ozone–friendly propellants," *Spray Technol. Market,* 4:26–29 (1994).

Timsina et al., "Drug delivery to the respiratory tract using dry powder inhalers," *Int. J. Pharm.,* 101: 1–13 (1994).

Turner, J. and S. Hering, "Greased and oiled substrates as bounce–free impaction surfaces," *J. Aerosol Sci.,* 18: 215–224 (1987).

* Vincent, *Aerosol Science for Industrial Hygientists,* Pergamon Press, NY (1995).

Visser, "An Invited Review: Van der Waals and Other Cohesive Forces Affecting Powder Fluidization," *Powder Technology* 58: 1–10 (1989).

Wall, "Pulmonary Absorption of Peptides and Proteins," *Drug Delivery,* 2:1–20 (1995).

Warheit and Hartsky, "Role of alveolar macrophage chemotaxis and phagocytosis in pulmonary clearance to inhaled particles: Comparisons among rodent species," *Microscopy Res. Tech.,* 26: 412–422 (1993).

Wheatley, et al. "Contrast agents for diagnostic ultrasound: development and evaluation of polymer–coated microbubbles" *Biomaterials* 11: 713–717(1990).

* Weibel, *Morphometry of the Human Lung,* New York: Academic Press (1963).

Wichert, et al. Low molecular weight PLA: a suitable polymer for pulmonary administered microparticles? *J. Microencapsulation,* 10: 195–207 (1993).

Wong and Suslick, "Sonochemically produced hemoglobin microbubbles," *Mat. Res. Soc. Symp. Proc.,* 372:89–95 (1995).

Zanen et al., "The optimal particle size for β–adrenergic aerosols in mild asthmatics," *Int. J. Pharm.,* 107: 211–217 (1994).

Zanen et al., "The optimal particle size for parasympathicolytic aerosols in mild asthmatics" *Int. J. Pharm.,* 114:111–115 (1995).
Zeng, et al. "Tetrandrine delivery to the lung: The optimisation of albumin microsphere preparation by central composite design" *Int. J. Pharm.,* 109: 135–145 (1994).
Zeng et al., "The controlled delivery of drugs to the lung," *Int. J. Pharm.,* 124:149–164 (1995).
Adjei and Garren, "Pulmonary Delivery of Peptide Drugs: Effect of Particle Size on Bioavailability of Leuprolide Acetate in Healthy Male Volunteers," *J. Pharm. Res.,* 7(6): 565–569 (1990).
Allen, et al. "Subcutaneous administration of liposomes: a comparison with the intravenous and intraperitoneal routes of injection" *Biochim. Biophys. Acta* 1150: 9–16 (1993).
Altschuler et al., "Aerosol deposition in the human respiratory tract," *Am. Med. Assoc. Arch. Indust. Health* 15:293–303 (1957).
Anderson, "Human Deposition and Clearance of 6 micrometer Particles Inhaled with an Extremely Low Flow Rate" *Exp. Lung Res.* 21(1): 187–195 (1995).
Anderson et al., "Effect of Cystic Fibrosis on Inhaled Aerosol Boluses," *Am. Rev. Respir. Dis.,* 140: 1317–1324 (1989).
Barrera et al., "Synthesis and RGD Peptide Modification of a New Biodegradable Copolymer: Poly(lactic acid–co–l-ysine)," *J. Am. Chem. Soc.,* 115:11010 (1993).
Beck, et al., "A new Long–Acting Injectable Microcapsule System for the Administration of Progesterone", *Fertility and Sterility* 31(5): 545–551 (1979).
Benita et al., "Characterization of drug–loaded poly(d,l–lactide) microspheres," *J. Pharm. Sci.* 73, 1721–1724 (1984).
Blackett and Buckton, "A Microcalorimetric Investigation of the Interaction of Surfactants with Crystalline and Partially Crystalline Salbutamol Sulphate in a Model Inhalation Aerosol System," *Pharmaceutical Research* 12(11):1689–1693 (1995).
Brain, "Physiology and Pathophysiology of Pulmonary Macrophages," in The Reticuloendothelial System, Reichard and Filkins, Eds., Plenum Press, New York, pp. 315–327 (1985).
Brown, et al. "Propellant–driven aerosols of functional proteins as potential therapeutic agents in the respiratory tract" *Immunopharmacology* 28:241–257 (1994).
Byron, "Determinants of drug and polypeptide bioavailability from aerosols delivered to the lung," *Adv. Drug. Del. Rev.,* 5: 107–132 (1990).
Carroll, et al. "Gelatin Encapsulated Nitrogen Microbubbles as Ultrasonic Contrast Agents" *Investigative Radiology* 15: 260–266 (1980).
Carroll, et al. "Ultrasonic Contrast Enhancement of Tissue by Encapsulated Microbubbles" *Radiology* 143:747–750 (1982).
Ch'ng, et al. :Bioadhesive Polymers as Platforms for Oral Controlled Drug Delivery II: Synthesis and Evaluation of Some Swelling, Water–Insoluble Bioadhesive Polymers *J. Pharm Sci* 74(4):399–405 (1985).
Clark, et al. "Dependence of Pulmonary Absorption Kinetics on Aerosol Particle Size" *Zeitschrift fur Erkankungren der Atmungsorgane* 166: 13–24 (1986).
Clark and Egan, "Modeling the deposition of inhaled powdered drug aerosols," *J. Aerosol Sci.,* 25:175–186 (1994).
Clay et al., "Effect of aerosol particle size on bronchodilation with nebulized terbutaline in asthmatic subjects," *Thorax* 41:364–368 (1986).
Cohen et al., "Controlled Delivery Systems for Proteins Based on Poly(Lactic/Glycolic Acid) Microspheres," *Pharm. Res.,* 8(6): 713–720 (1991).
Colthorpe et al., "The Pharmacokinetics of Pulmonary–Delivered Insulin: A Comparison of Intratracheals and Aerosol Administration to the Rabbit," *Pharm. Res.* 9:764 (1992).
Daly et al., "The Preparation of N–Carboxyanhydrides of α–Amino Acids Using Bis(Trichloromethyl)Carbonate," *Tetrahedron Lett.,* 29:5859 (1988).
Damms and Bains, "The Cost of Delivering Drugs without Needles,", *J. Controlled Release,* 8–11 (1996).
Darquenne, et al. "Two and three–dimensional simulations of aerosol transport and deposition in alveolar zone of human lung" Journal of Applied Physiology.
Davies, et al "Breathing of half–micron aerosols I. Experimental" *J. App. Physiol.* 32: 591–600 (1972).
Davis, et al. "Polymeric microspheres as drug carries" *Biomaterials* 9:111–115 (1988).
Davis, et al. "Microspheres as Controlled Release Systems for Parenteral and Nasal Administration", *Controlled Release Technology* Chapter 15, pp. 201–213 (1987).
Dorries and Valberg, "Heterogeneity of phagocytosis for inhaled versus instilled material," *Am. Rev. Resp. Disease,* 146: 831–837 (1991).
* Doubrow, M., Ed., "Microcapsules and Nanoparticles in Medicine and Pharmacy," CRC Press, Boca Raton, (1992).
Edwards, et al. "Large Porous Particles for Pulmonary Drug Delivery" *Science,* 276: 1868–71 (1997).
Edwards, "The macrotransport of aerosol particles in the lung: Aerosol deposition phenomena," *J. Aerosol Sci.,* 26: 293–317 (1995).
Eldridge et al., "Biodegradable microspheres as a vaccine delivery system," *Mol. Immunol.,* 28: 287–294 (1991).
Feinstein, et al. "Two–Dimensional Contrast Echocardiography. I. In Vitro Development and Quantitative Analysis of Echo Contrast Agents" *JACC* 3(1): 14–20 (1984).
Ferin, "Pulmonary Retention of Ultrafine and Fine Particles in Rats" *Am. J. Respir. Cell Mol. Biol.* 6: 535–542 (1992).
Findeisen, "Uber das Absetzen kleiner in der Luft suspendierter Teilchen in der menshlichen Lunge bei der Atmung," *Pflugers Arch. D. Ges. Physiol.* 236:367–379 (1935).
French, Edwards, and Niven, "The influence of formulation on emission, deaggregation and deposition of dry powders for inhalation," *J. Aerosol Sci.,* 27: 769–783 (1996).
Ganderton, "The generation of respirable clouds from coarse powder aggregates," *J. Biopharmaceutical Sciences,* 3:101–105 (1992).
Gehr et al., "Surfactant and inhaled particles in the conducting airways: Structural, stereological, and biophysical aspects," *Microscopy Res. and Tech.,* 26: 423–436 (1993).
Gerrity et al., "Calculated deposition of inhaled particles in the airway generations of normal subjects," *J. Appl. Phys.,* 47:867–873 (1979).
Gonda, "Aerosols for delivery of therapeutic and diagnostic agents to the respiratory tract," in *Critical Reviews in Therapeutic Drug Carrier Systems* 6:273–313 (1990).
Gonda, "Preface. Major issues and future prospects in the delivery of therapeutic and diagnostic agents to the respiratory tract," *Adv. Drug Del. Rev.,* 5: 1–9 (1990).
Gonda, "Physico–chemical principles in aerosol delivery," in *Topics in Pharmaceutical Sciences* 1991, Crommelin, D.J. and K.K. Midha, Eds., Medpharm Scientific Publishers, Stuttgart, pp. 95–117, 1992.

Gonda, "Targeting by deposition," in *Pharmaceutical Inhalation Aerosol Technology* (ed. A.J. Hickey), Marcel Dekkar Inc., New York, 1992.

Gurney, et al. Bioadhesive intraoral release systems: design, testing and analysis *Biomaterials* 5: 336–340 (1984).

Heyder et al., "Deposition of Particles in the Human Respiratory Tract in the Size Range 0.005–15 micrometers," *J. Aerosol Sci.,* 17: 811–825 (1986).

Heyder and Rudolf, "Mathematical models of particle deposition in the human respiratory tract," *J. Aerosol Sci.,* 15:697–707 (1984).

Heyder et al., "Total Deposition of Aerosol Particles in the Human Respiratory Tract for Nose and Mouth Breathing," *J. Aerosol Sci.,* 6:311–328 (1975).

Hickey et al., "Use of particle morphology to influence the delivery of drugs from dry powder aerosols," *J. Biopharmaceutical Sci.,* 2(1/2):107–113 (1992).

Hirano et al, "Pulmonary clearance and Toxicity of Zinc Oxide Instilled into the Rat Lung," *Toxicology* 63:336–342 (1989).

Hrkach et al., "Synthesis of Poly(L–lactic acid–co–L–lysine) graft copolymers," *Macromolecules,* 28:4736–4739 (1995).

Hrkach et al., "Poly(L–Lactic acid–co–amino acid) Graft Copolymers: A Class of Functional Biodegradable Biomaterials" in Hydrogels and Biodegradable Polymers for Bioapplications, ACS Symposium Series No. 627, Raphael M. Ottenbrite et al., Eds., American Chemical Society, Chapter 8, pp. 93–101, 1996.

Illum, "Bioadhesive microspheres as a potential nasal drug delivery system" *Int. J Pharm.* 39: 189–199 (1987).

Illum, "Microspheres as a Potential Controlled Release Nasal Drug Delivery System," *Delivery Systems for Peptide Drugs,* NY: Plenum, 1986.

Johnson et al., "Delivery of Albuterol and Ipratropiumbromide from Two Nebulizer Systems in Chronic Stable Asthma," *Chest,* 96, 6–10, 1989.

Kao, et al. "Interactions of liposomes with the Reticuloendothelial System" *Biochim. Biophys. Acta.* 677: 453–461 (1981).

Kassem and Ganderton, "The Influence of Carrier Surface on the Characteristics of Inspirable Powder Aerosols," *J. Pharm. Pharmacol.,* 42 (Supp):11 (1990).

Kawaguchi et al., "Phagocytosis of latex particles by leukocytes. I. Dependence of phagocytosis on the size and surface potential of particles," *Biomaterials* 7: 61–66 (1986).

Kobayashi, S., et al., "Pulmonary Delivery of Salmon Calcitonin Dry Powders Containing Absorption Enhancers in Rats" *Pharm. Res.,* 13(1): 80–83 (1996).

Kohler, "Aerosols for Systemic Treatment" *Lung* Suppl: 677–684 (1990).

Komada et al., "Intratracheal Delivery of Peptide and Protein Agents: Absorption from Solution and Dry Powder by Rat Lung," *J. Pharm. Sci.* 83(6):863–867 (Jun., 1994).

Krenis and Strauss, "Effect of Size and Concentration of Latex Particles on Respiration of Human Blood Leucocytes," *Proc. Soc. Exp. Med.,* 107:748–750 (1961).

Kricheldorf, H. R. in *Models of Biopolymers by Ring–Opening Polymerization,* Penczek, S., Ed., CRC Press, Boca Raton, 1990, Chapter 1.

Kricheldorf, H. R. *α–Aminoacid–N–Carboxy–Anhydrides and Related Heterocycles,* Springer–Verlag, Berlin, 1987.

Kwok, et al. "Production of 5–15 micrometer Diameter Alginate Polylysine Microcapsules by an Air–Atomization Technique," *Pharm Res.* 8(3):341–344 (1991).

Lai, et al. "Protection Against Mycoplasma pulminosis Infection by Genetic Vaccination" *DNA and Cell Biology* 14(7): 643–651 (1995).

Lai et al., "Sustained bronchodilation with isoproterenol poly(glycolide–co–lactide) microspheres," *Pharm. Res.,* 10(1) 119–125 (1993).

Landahl, "On the removal of air–borne droplets by the human respiratory tract: I. The lung, " *Bull. Math. Biophys.,* 12:43–56 (1950).

Langer, "New Methods of Drug Delivery," *Science,* 249:1527–1533 (1990).

LeCorre et al., Preparation and characterization of bupivacaine–loaded polylactide and polylactide–co–glycolide microspheres, *Int. J. Pharmaceutics,* 107:41–49 (1994).

Leone–Bay et al., "Microsphere formation in a series of derivatized α–amino acids: Properties, molecular modeling and oral delivery of salmon calcitonin," *J. Med. Chem.,* 38:4257–4262 (1995).

Liu et al., "Pulmonary Delivery of Free and Liposomal Insulin," *Pharm. Res.* 10(2):228–232 (1993).

Liu et al., "Moisture–induced aggregation of lyophilized proteins in the solid state," *Biotechnol. Bioeng.,* 37: 177–184 (1991).

Martonen, "Mathematical model for the selective deposition of inhaled pharmaceuticals", *J. Pharm. Sci.,* 82(12):1191–1198 (1993).

Masinde and Hickey, "Aerosolized aqueous suspensions of poly(L–lactic acid) microspheres," *Int. J. Pharmaceutics,* 100:123–131 (1993).

Mathiowitz et al., "Polyanhydride Microspheres. IV. Morphology and Characterization of Systems Made by Spray Drying" *J. Appl. Polymer Sci.* 45, 125–134 (1992).

Mathiowitz et al., "Novel Microcapsules for delivery Systems" *Reactive Polymers,* 6:275 (1987).

Mathiowitz et al., "Morphology of Polyanhydride Microsphere Delivery Systems" *Scanning Microscopy* 4: 329–340 (1990).

Mathiowitz et al., "Polyanhydride Microspheres as Drug Carriers. II. Microencapsulation by Solvent Removal" *J. Appl. Polymer Sci.* 35, 755–774 (1988).

Mathiowitz, et al., "Polyanhydride Microspheres as Drug Carriers I. Hot–Melt Encapsulation" *J. Controlled Release* 5, 13–22 (1987).

Menache, et al. "Particle Inhalability Curves for Humans and Small Laboratory Animals" *Annals of Occupational Hygiene* 39(3): 317–328 (1995).

Moren, "Aerosol dosage forms and formulations," in: *Aerosols in Medicine. Principles, Diagnosis and Therapy,* Moren, et al., Eds, Elsevier, Amsterdam, 1985.

Morimoto and Adachi, "Pulmonary Uptake of Liposomal Phosphatidylcholine Upon Intratracheal Administration to Rats," *Chem. Pharm. Bull.* 30(6):2248–2251 (1982).

Mulligan, "The Basic Science of Gene Therapy," *Science,* 260: 926–932 (1993).

Mumenthaler et al., "Feasibility Study on Spray–Drying Protein Pharmaceuticals: Recombinant Human Growth Hormone and Tissue–Type Plasminogen Activator," *Pharm. Res.,* 11: 12–20 (1994).

Newman, "Therapeutic inhalation agents and devices" *Postgraduate Medicine* 76(5):194–207 (1984).

Newman, "Aerosol Deposition Considerations in Inhalation Therapy" *Chest* 88(2) 153–160 (1985).

* New, R.R.C., "Characterization of Liposomes," in *Liposomes: A Practical Approach,* R. New, Editor, IRL Press, New York, 105–161 (1990).
Niven, et al. "Solute Absorpion from the Airways of the Isolated Rat Lung. III. Absorption of Several Peptidase–Resistant, Synthetic Polypeptides: Poly–(2–Hydroxyethyl)–Aspartamides" *Pharm. Res.,* 7(10) 990–994 (1990).
Niven, et al., "The Pulmonary Absorption of Aerosolized and Intratracheally Instilled rhG–CSF and monoPEGylated rhG–CSF," *Pharm. Res.,* 12(9): 1343–1349 (1995).
Niwa, et al. "Aerosolization of lactice–glycolide copolymer (PLGA) nanospheres for pulmonary delivery ofm peptide–drugs," *Yakugaku Zasshi* 115(9): 732–741 (1995).
Ogiwara, "Clearance and Maximum removal rate of Liposomes in Normal and Impaired Liver of Rat" *Gastrenterologia Japonica* 19(1) 34–40 (1984).
Okumura et al., "Intratracheal delivery of insulin. Absorption from solution and aerosol by rat lung," *Int. J. Pharmaceutics,* 88:63–73 (1992).
Patton and Platz, "(D) Routes of Delivery: Case Studies (2) Pulomonary delivery of peptides and proteins," *Adv. Drug Del. Rev.,* 8: 179–196 (1992).
Patton et al., "Bioavailability of pulmonary delivered peptides and proteins: α–interferon, calcitonins and parathyroid hormones," *J. Controlled Release,* 28: 79–85 (1994).
* Pavia, D. "Lung Mucociliary Clearance," in *Aerosols and the Lung: Clinical and Experimental Aspects,* Clarke, S.W. and Pavia, D., Eds., Butterworths, London, 1984.
* Phalen, *Inhalation Studies: Foundations and Techniques.* CRC Press (Boca Raton, Fl), 1984.
Pinkeron et al., "Aerosolized fluorescent microspheres detected in the lung using confocal scanning laser microscopy," *Microscopy Res. and Techn.,* 26:437–443 (1993).
Rudt and Muller, "In vitro Phagocytosis Assay of Nano– and Microparticles by chemiluminescence. I. Effect of Analytical Parameters, Particle Size and Particle Concentration," *J. Contr. Rel.,* 22: 263–272 (1992).
Rudt et al., "In vitro phagocytosis assay of nano– and microparticles by chemiluminescence. IV. Effect of surface modification by coating of particles with poloxamine and Antarox CO on the phagocytic uptake," *J. Contr. Rel.* 25:123 (1993).
Ruffin et al., "The Preferential Deposition of Inhaled Isoproterenol and Propanolol in Asthmataic Patients," *Chest* 80:904–907 (1986).

PREPARATION OF PARTICLES FOR INHALATION

This application claims the benefit of U.S. provisional application Ser. No. 60/059,004 filed Sep. 15, 1997, and a continuation of Ser. No. 08/784,421 filed Jan. 16, 1997.

BACKGROUND OF THE INVENTION

The present application relates generally to particles for use in drug delivery to the pulmonary system.

Aerosols for the delivery of therapeutic agents to the respiratory tract have been described, for example, Adjei, A. and Garren, *J. Pharm. Res.,* 7: 565–569 (1990); and Zanen, P. and Lamm, J. -W. J. *Int. J. Pharm.,* 114: 111–115 (1995). The respiratory tract encompasses the upper airways, including the oropharynx and larynx, followed by the lower airways, which include the trachea followed by bifurcations into the bronchi and bronchioli. The upper and lower airways are called the conducting airways. The terminal bronchioli then divide into respiratory bronchioli which then lead to the ultimate respiratory zone, the alveoli, or deep lung. Gonda, I. "Aerosols for delivery of therapeutic and diagnostic agents to the respiratory tract," in *Critical Reviews in Therapeutic Drug Carrier Systems,* 6:273–313 (1990). The deep lung, or alveoli, are the primary target of inhaled therapeutic aerosols for systemic drug delivery.

Inhaled aerosols have been used for the treatment of local lung disorders including asthma and cystic fibrosis (Anderson et al., *Am. Rev. Respir. Dis.,* 140: 1317–1324 (1989)) and have potential for the systemic delivery of peptides and proteins as well (Patton and Platz, *Advanced Drug Delivery Reviews,* 8: 179–196 (1992)). However, pulmonary drug delivery strategies present many difficulties for the delivery of macromolecules; these include protein denaturation during aerosolization, excessive loss of inhaled drug in the oropharyngeal cavity (often exceeding 80%), poor control over the site of deposition, lack of reproducibility of therapeutic results owing to variations in breathing patterns, the frequent too-rapid absorption of drug potentially resulting in local toxic effects, and phagocytosis by lung macrophages.

Considerable attention has been devoted to the design of therapeutic aerosol inhalers to improve the efficiency of inhalation therapies. Tinsina et. al., *Int. J. Pharm.,* 101: 1–13 (1995); and Tansey, I. P., *Spray Technol. Market,* 4: 26–29 (1994). Attention has also been given to the design of dry powder aerosol surface texture, regarding particularly the need to avoid particle aggregation, a phenomenon which considerably diminishes the efficiency of inhalation therapies. French, D. L., Edwards, D. A. and Niven, R. W., *J. Aerosol Sci.,* 27: 769–783 (1996). Dry powder formulations ("DPFs") with large particle size have improved flowability characteristics, such as less aggregation (Visser, J., *Powder Technology* 58: 1–10 (1989)), easier aerosolization, and potentially less phagocytosis. Rudt, S. and R. H. Muller, J. *Controlled Release,* 22: 263–272 (1992); Tabata, Y. and Y. Ikada, *J. Biomed. Mater. Res.,* 22: 837–858 (1988). Dry powder aerosols for inhalation therapy are generally produced with mean diameters primarily in the range of less than 5 μm. Ganderton, D., *J. Biopharmaceutical Sciences,* 3:101–105 (1992); and Gonda, I. "Physico-Chemical Principles in Aerosol Delivery," in *Topics in Pharmaceutical Sciences* 1991, Crommelin, D. J. and K. K. Midha, Eds., Medpharm Scientific Publishers, Stuttgart, pp. 95–115, 1992. Large "carrier" particles (containing no drug) have been co-delivered with therapeutic aerosols to aid in achieving efficient aerosolization among other possible benefits. French, D. L., Edwards, D. A. and Niven, R. W., *J. Aerosol Sci.,* 27: 769–783 (1996).

The human lungs can remove or rapidly degrade hydrolytically cleavable deposited aerosols over periods ranging from minutes to hours. In the upper airways, ciliated epithelia contribute to the "mucociliary escalator" by which particles are swept from the airways toward the mouth. Pavia, D. "Lung Mucociliary Clearance," in *Aerosols and the Lung: Clinical and Experimental Aspects,* Clarke, S. W. and Pavia, D., Eds., Butterworths, London, 1984. Anderson et al., *Am. Rev. Respir. Dis.,* 140: 1317–1324 (1989). In the deep lungs, alveolar macrophages are capable of phagocytosing particles soon after their deposition. Warheit, M. B. and Hartsky, M. A., *Microscopy Res. Tech.,* 26: 412–422 (1993); Brain, J. D., "Physiology and Pathophysiology of Pulmonary Macrophages," in *The Reticuloendothelial System,* S. M. Reichard and J. Filkins, Eds., Plenum, New York, pp. 315–327, 1985; Dorries, A. M. and Valberg, P. A., *Am. Rev. Resp. Disease* 146: 831–837 (1991); and Gehr, P. et al. *Microscopy Res. and Tech.,* 26: 423–436 (1993). As the diameter of particles exceeds 3 μm, there is increasingly less phagocytosis by macrophages. Kawaguchi, H. et al., *Biomaterials* 7: 61–66 (1986); Krenis, L. J. and Strauss, B., *Proc. Soc. Exp. Med.,* 107:748–750 (1961); and Rudt, S. and Muller, R. H., *J. Contr. Rel.,* 22: 263–272 (1992). However, increasing the particle size also has been found to minimize the probability of particles (possessing standard mass density) entering the airways and acini due to excessive deposition in the oropharyngeal or nasal regions. Heyder, J. et al., *J. Aerosol Sci.,* 17: 811–825 (1986).

Local and systemic inhalation therapies can often benefit from a relatively slow controlled release of the therapeutic agent. Gonda, I., "Physico-chemical principles in aerosol delivery," in: *Topics in Pharmaceutical Sciences* 1991, D. J. A. Crommelin and K. K. Midha, Eds., Stuttgart: Medpharm Scientific Publishers, pp. 95–117 (1992). Slow release from a therapeutic aerosol can prolong the residence of an administered drug in the airways or acini, and diminish the rate of drug appearance in the bloodstream. Also, patient compliance is increased by reducing the frequency of dosing. Langer, R., *Science,* 249:1527–1533 (1990); and Gonda, I. "Aerosols for delivery of therapeutic and diagnostic agents to the respiratory tract," in *Critical Reviews in Therapeutic Drug Carrier Systems* 6:273–313 (1990).

Controlled release drug delivery to the lung may simplify the way in which many drugs are taken. Gonda, I., *Adv. Drug Del. Rev.,* 5: 1–9 (1990); and Zeng, X. et al., *Int. J. Pharm.,* 124: 149–164 (1995). Pulmonary drug delivery is an attractive alternative to oral, transdermal, and parenteral administration because self-administration is simple, the lungs provide a large mucosal surface for drug absorption, there is no first-pass liver effect of absorbed drugs, and there is reduced enzymatic activity and pH mediated drug degradation compared with the oral route. Relatively high bioavailability of many molecules, including macromolecules, can be achieved via inhalation. Wall, D. A., *Drug Delivery,* 2: 1–20 1995); Patton, J. and Platz, R., *Adv. Drug Del. Rev.,* 8: 179–196 (1992); and Byron, P., *Adv. Drug. Del. Rev.,* 5: 107–132 (1990). As a result, several aerosol formulations of therapeutic drugs are in use or are being tested for delivery to the lung. Patton, J. S., et al., *J. Controlled Release,* 28: 79–85 (1994); Damms, B. and Bains, W., *Nature Biotechnology* (1996); Niven, R. W., et al., *Pharm. Res.,* 12(9): 1343–1349 (1995); and Kobayashi, S., et al., *Pharm. Res.,* 13(1): 80–83 (1996).

Drugs currently administered by inhalation come primarily as liquid aerosol formulations. However, many drugs and excipients, especially proteins, peptides (Liu, R., et al., *Biotechnol. Bioeng.,* 37:177–184 (1991)), and biodegradable carriers such as poly(lactide-co-glycolides) (PLGA), are unstable in aqueous environments for extended periods of time. This can make storage as a liquid formulation problematic. In addition, protein denaturation can occur during aerosolization with liquid formulations. Mumenthaler, M., et al., *Pharm. Res.,* 11: 12–20 (1994). Considering these and other limitations, dry powder formulations (DPF's) are gaining increased interest as aerosol formulations for pulmonary delivery. Damms, B. and W. Bains, *Nature Biotechnology* (1996); Kobayashi, S., et al., *Pharm. Res.,* 13(1): 80–83 (1996); and Timsina, M., et al., *Int. J. Pharm.,* 101: 1–13 (1994). However, among the disadvantages of DPF's is that powders of ultrafine particulates usually have poor flowability and aerosolization properties, leading to relatively low respirable fractions of aerosol, which are the fractions of inhaled aerosol that escape deposition in the mouth and throat. Gonda, I., in *Topics in Pharmaceutical Sciences* 1991, D. Crommelin and K. Midha, Editors, Stuttgart: Medpharm Scientific Publishers, 95–117 (1992). A primary concern with many aerosols is particulate aggregation caused by particle-particle interactions, such as hydrophobic, electrostatic, and capillary interactions. An effective dry-powder inhalation therapy for both short and long term release of therapeutics, either for local or systemic delivery, requires a powder that displays minimum aggregation, as well as a means of avoiding or suspending the lung's natural clearance mechanisms until drugs have been effectively delivered.

There is a need for improved inhaled aerosols for pulmonary delivery of therapeutic agents. There is a need for the development of drug carriers which are capable of delivering the drug in an effective amount into the airways or the alveolar zone of the lung. There further is a need for the development of drug carriers for use as inhaled aerosols which are biodegradable and are capable of controlled release of drug within the airways or in the alveolar zone of the lung. There also is a need for particles for pulmonary drug delivery with improved aerosolization properties.

It is therefore an object of the present invention to provide improved carriers for the pulmonary delivery of therapeutic agents. It is a further object of the invention to provide inhaled aerosols which are effective carriers for delivery of therapeutic agents to the deep lung. It is another object of the invention to provide carriers for pulmonary delivery which avoid phagocytosis in the deep lung. It is a further object of the invention to provide carriers for pulmonary drug delivery which are capable of biodegrading and releasing the drug at a controlled rate. It is yet another object of the invention to provide particles for pulmonary drug delivery with improved aerosolization properties and optimized particle-particle interactions.

SUMMARY OF THE INVENTION

Particles incorporating a surfactant and/or a hydrophilic or hydrophobic complex of a positively or negatively charged therapeutic agent and a charged molecule of opposite charge for delivery of therapeutic or diagnostic agents to the pulmonary system, and methods for their synthesis and administration, are provided. Exemplary surfactants include naturally occurring phosphatidylcholines, such as dipalmitoylphosphatidylcholine ("DPPC"). Exemplary hydrophilic or hydrophobic complexes include insulin (negatively charged) and protamine (positively charged). In a preferred embodiment, the particles are aerodynamically light particles, which are made of a biodegradable material, and have a tap density less than 0.4 g/cm$^3$. The "aerodynamically light" particles generally have a mean diameter between 5 $\mu$m and 30 $\mu$m. The tap density less than 0.4 g/cm$^3$ and mean diameter between 5 $\mu$m and 30 $\mu$m, are designed to yield particles with an aerodynamic diameter between approximately one and five microns, preferably between approximately one and three microns. The particles may be formed of biodegradable materials such as biodegradable polymers, proteins, or other water soluble or non-water soluble materials. Particles can also be formed of water-soluble excipients, such as trehalose or lactose, or proteins, such as the proteins to be delivered. In one embodiment, the particles include only a therapeutic or diagnostic agent to be delivered to a patient in a complex with another charged molecule. In a second embodiment, the particles include only the agent and a surfactant. In a third embodiment, particles include surfactant and charged molecules forming a complex, which provides for sustained release.

The particles can be used for enhanced delivery of a therapeutic agent to the airways or the alveolar region of the lung. The particles may be effectively aerosolized for administration to the respiratory tract to permit systemic or local delivery of a wide variety of therapeutic agents. They also optionally may be co-delivered with larger carrier particles, not carrying a therapeutic agent, having, for example, a mean diameter ranging between about 50 $\mu$m and 100 $\mu$m. The particles can be used to form a composition that includes the particles and a pharmaceutically acceptable carrier for administration to a patient, preferably for administration via inhalation.

DETAILED DESCRIPTION OF THE INVENTION

Figure 1:
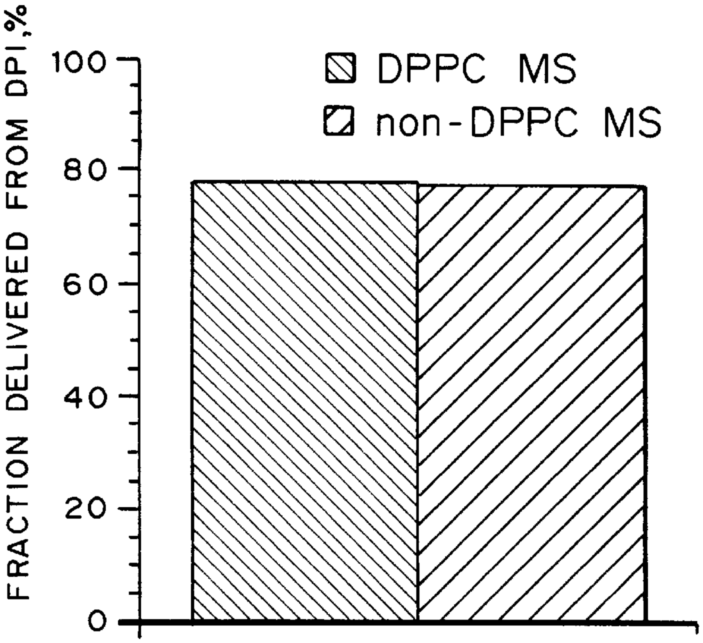
FIG. 1 is a graph comparing the mass fraction of the initial dose that is released from a dry powder inhaler device, after in vitro aerosolization of poly (D,L-lactic-co-glycolic acid) ("PLGA") microspheres made by a double emulsion procedure with and without the incorporation of L-$\alpha$-phosphatidylcholine dipalmitoyl ("DPPC").

Particles incorporating a surfactant and/or a hydrophilic or hydrophobic complex of a positively or negatively charged therapeutic or diagnostic agent and a charged molecule of opposite charge for delivery to the pulmonary system, and methods for their synthesis and administration are provided. The particles can, but need not include a therapeutic or diagnostic agent. In one embodiment, the particles include either only a therapeutic or diagnostic agent for delivery to a patient. In a second embodiment, the particles include a therapeutic or diagnostic the agent and a surfactant.

The particles have a tap density less than 0.4 g/cm$^3$ and a mean diameter between 5 μm and 30 μm, which in combination yield an aerodynamic diameter of between one and five microns, preferably between one and three microns. The aerodyanamic diameter is calculated to provide for maximum deposition within the lungs, previously achieved by the use of very small particles of less than five microns in diameter, preferably between one and three microns, which are then subject to phagocytosis. Selection of particles which have a larger diameter, but which are sufficiently light (hence the characterization "aerodynamically light"), results in an equivalent delivery to the lungs, but the larger size particles are not phagocytosed. Improved delivery can be obtained by using particles with a rough or uneven surface relative to those with a smooth surface. The presence of a surfactant minimizes aggregation of the particles. The presence of a complex of the therapeutic agent with a molecule of opposite charge provides for sustained release of the agent.

The particles can be used for controlled systemic or local delivery of therapeutic or diagnostic agents to the respiratory tract via aerosolization. Administration of the particles to the lung by aerosolization permits deep lung delivery of relatively large diameter therapeutic aerosols, for example, greater than 5 μm in mean diameter. The particles can be fabricated with a rough surface texture to reduce particle agglomeration and improve flowability of the powder. The particles have improved aerosolization properties. The particle can be fabricated with features which enhance aerosolization via dry powder inhaler devices, and lead to lower deposition in the mouth, throat and inhaler device.

The particles can be used to form a composition that includes the particles and a pharmaceutically acceptable carrier for administration to a patient, preferably for administration via inhalation. Suitable carriers include those typically used for inhalation therapy. Those of skill in the art can readily determine an appropriate pharmaceutically acceptable carrier for use in administering particles via inhalation.

Particle Materials

The particles can be prepared entirely from a therapeutic or diagnostic agent, or from a combination of the agent and a surfactant. The particles preferably are biodegradable and biocompatible, and optionally are capable of biodegrading at a controlled rate for delivery of a therapeutic or diagnostic agent. The particles can be made of a variety of materials. Both inorganic and organic materials can be used. For example, ceramics may be used. Polymeric and non-polymeric materials, such as fatty acids, may be used to form aerodynamically light particles. Other suitable materials include, but are not limited to, gelatin, polyethylene glycol, trehalose, and dextran. Particles with degradation and release times ranging from seconds to months can be designed and fabricated, based on factors such as the particle material. Different properties of the particle which can contribute to the aerodynamic lightness include the composition forming the particle, and the presence of irregular surface structure, or pores or cavities within the particle.

Polymeric Particles

Polymeric particles may be formed from any biocompatible, and preferably biodegradable polymer, copolymer, or blend. Preferred polymers are those which are capable of forming aerodynamically light particles having a tap density less than about 0.4 g/cm$^3$, a mean diameter between 5 μm and 30 μm and an aerodynamic diameter between approximately one and five microns, preferably between one and three microns. The polymers may be tailored to optimize different characteristics of the particle including: i) interactions between the agent to be delivered and the polymer to provide stabilization of the agent and retention of activity upon delivery; ii) rate of polymer degradation and, thereby, rate of drug release profiles; iii) surface characteristics and targeting capabilities via chemical modification; and iv) particle porosity.

Surface eroding polymers such as polyanhydrides may be used to form the particles. For example, polyanhydrides such as poly[(p-carboxyphenoxy)-hexane anhydride] (PCPH) may be used. Biodegradable polyanhydrides are described in U.S. Pat. No. 4,857,311.

In another embodiment, bulk eroding polymers such as those based on polyesters including poly(hydroxy acids) can be used. For example, polyglycolic acid (PGA), polylactic acid (PLA), or copolymers thereof may be used to form the particles. The polyester may also have a charged or functionalizable group, such as an amino acid. In a preferred embodiment, particles with controlled release properties can be formed of poly(D,L-lactic acid) and/or poly(D,L-lactic-co-glycolic acid) ("PLGA") which incorporate a surfactant such as DPPC.

Other polymers include polyamides, polycarbonates, polyalkylenes such as polyethylene, polypropylene, poly (ethylene glycol), poly(ethylene oxide), poly(ethylene terephthalate), poly vinyl compounds such as polyvinyl alcohols, polyvinyl ethers, and polyvinyl esters, polymers of acrylic and methacrylic acids, celluloses and other polysaccharides, and peptides or proteins, or copolymers or blends thereof. Polymers may be selected with or modified to have the appropriate stability and degradation rates in vivo for different controlled drug delivery applications.

In one embodiment, aerodynamically light particles are formed from functionalized polyester graft copolymers, as described in Hrkach et al., *Macromolecules,* 28:4736–4739 (1995); and Hrkach et al., "Poly(L-Lactic acid-co-amino acid) Graft Copolymers: A Class of Functional Biodegradable Biomaterials" in *Hydrogels and Biodegradable Polymers for Bioapplications,* ACS Symposium Series No. 627, Raphael M. Ottenbrite et al., Eds., American Chemical Society, Chapter 8, pp. 93–101, 1996.

Materials other than biodegradable polymers may be used to form the particles. Suitable materials include various non-biodegradable polymers and various excipients. The particles also may be formed of a therapeutic or diagnostic agent and surfactant alone. In one embodiment, the particles may be formed of the surfactant and include a therapeutic or diagnostic agent, to improve aerosolization efficiency due to reduced particle surface interactions, and to potentially reduce loss of the agent due to phagocytosis by alveolar macrophages.

Excipients

In addition to a therapeutic or diagnostic agent (or possibly other desired molecules for delivery), the particles can include, and preferably, do include, one or more of the following excipients; a sugar, such as lactose, a protein, such as albumin, and/or a surfactant.

Complex Forming Materials

If the agent to be delivered is negatively charged (such as insulin), protamine or other positively charged molecules can be added to provide a lipophilic complex which results in the sustained release of the negatively charged agent. Negatively charged molecules can be used to render insoluble positively charged agents.

Surfactants

Surfactants which can be incorporated into particles to improve their aerosolization properties include phosphoglycerides. Exemplary phosphoglycerides include phosphatidylcholines, such as the naturally occurring surfactant, L-α-phosphatidylcholine dipalmitoyl ("DPPC"). The surfactants advantageously improve surface properties by, for example, reducing particle-particle interactions, and can render the surface of the particles less adhesive. The use of surfactants endogenous to the lung may avoid the need for the use of non-physiologic surfactants.

As used herein, the term "surfactant" refers to any agent which preferentially absorbs to an interface between two immiscible phases, such as the interface between water and an organic polymer solution, a water/air interface or organic solvent/air interface. Surfactants generally possess a hydrophilic moiety and a lipophilic moiety, such that, upon absorbing to microparticles, they tend to present moieties to the external environment that do not attract similarly-coated particles, thus reducing particle agglomeration. Surfactants may also promote absorption of a therapeutic or diagnostic agent and increase bioavailability of the agent.

As used herein, a particle "incorporating a surfactant" refers to a particle with a surfactant on at least the surface of the particle. The surfactant may be incorporated throughout the particle and on the surface during particle formation, or may be coated on the particle after particle formation. The surfactant can be coated on the particle surface by adsorption, ionic or covalent attachment, or physically "entrapped" by the surrounding matrix. The surfactant can be, for example, incorporated into controlled release particles, such as polymeric microspheres.

Providing a surfactant on the surfaces of the particles can reduce the tendency of the particles to agglomerate due to interactions such as electrostatic interactions, Van der Waals forces, and capillary action. The presence of the surfactant on the particle surface can provide increased surface rugosity (roughness), thereby improving aerosolization by reducing the surface area available for intimate particle-particle interaction. The use of a surfactant which is a natural material of the lung can potentially reduce opsonization (and thereby reducing phagocytosis by alveolar macrophages), thus providing a longer-lived controlled release particle in the lung.

Surfactants known in the art can be used including any naturally occurring surfactant. Other exemplary surfactants include diphosphatidyl glycerol (DPPG); hexadecanol; fatty alcohols such as polyethylene glycol (PEG); polyoxyethylene-9-lauryl ether; a surface active fatty acid, such as palmitic acid or oleic acid; sorbitan trioleate (Span 85); glycocholate; surfactin; a poloxomer; a sorbitan fatty acid ester such as sorbitan trioleate; tyloxapol and a phospholipid.

Materials Enhancing Sustained Release

If the molecules are hydrophilic and tend to solubilize readily in an aqueous environment, another method for achieving sustained release is to use cholesterol or very high surfactant concentration. This complexation methodology also applies to particles that are not aerodynamically light.

Formation of Particles

Formation of Polymeric Particles

Polymeric particles may be prepared using single and double emulsion solvent evaporation, spray drying, solvent extraction, solvent evaporation, phase separation, simple and complex coacervation, interfacial polymerization, and other methods well known to those of ordinary skill in the art. Particles may be made using methods for making microspheres or microcapsules known in the art, provided that the conditions are optimized for forming particles with the desired aerodynamic diameter, or additional steps are performed to select particles with the density and diameter sufficient to provide the particles with an aerodynamic diameter between one and five microns, preferably between one and three microns.

Methods developed for making microspheres for delivery of encapsulated agents are described in the literature, for example, as described in Doubrow, M., Ed., "Microcapsules and Nanoparticles in Medicine and Pharmacy," CRC Press, Boca Raton, 1992. Methods also are described in Mathiowitz and Langer, *J. Controlled Release* 5,13–22 (1987); Mathiowitz et al., *Reactive Polymers* 6, 275–283 (1987); and Mathiowitz et al., *J. Appl. Polymer Sci.* 35, 755–774 (1988). The selection of the method depends on the polymer selection, the size, external morphology, and crystallinity that is desired, as described, for example, by Mathiowitz et al., *Scanning Microscopy* 4: 329–340 (1990); Mathiowitz et al., *J. Appl. Polymer Sci.* 45, 125–134 (1992); and Benita et al., *J. Pharm. Sci.* 73, 1721–1724 (1984).

In solvent evaporation, described for example, in Mathiowitz et al., (1990), Benita; and U.S. Pat. No. 4,272,398 to Jaffe, the polymer is dissolved in a volatile organic solvent, such as methylene chloride. Several different polymer concentrations can be used, for example, between 0.05 and 1.0 g/ml. The therapeutic or diagnostic agent, either in soluble form or dispersed as fine particles, is added to the polymer solution, and the mixture is suspended in an aqueous phase that contains a surface active agent such as poly(vinyl alcohol). The aqueous phase may be, for example, a concentration of 1% poly(vinyl alcohol) w/v in distilled water. The resulting emulsion is stirred until most of the organic solvent evaporates, leaving solid microspheres, which may be washed with water and dried overnight in a lyophilizer. Microspheres with different sizes (between 1 and 1000 microns) and morphologies can be obtained by this method.

Solvent removal was primarily designed for use with less stable polymers, such as the polyanhydrides. In this method, the agent is dispersed or dissolved in a solution of a selected polymer in a volatile organic solvent like methylene chloride. The mixture is then suspended in oil, such as silicon oil, by stirring, to form an emulsion. Within 24 hours, the solvent diffuses into the oil phase and the emulsion droplets harden into solid polymer microspheres. Unlike the hot-melt microencapsulation method described for example in Mathiowitz et al., *Reactive Polymers,* 6:275 (1987), this method can be used to make microspheres from polymers with high melting points and a wide range of molecular weights. Microspheres having a diameter for example between one and 300 microns can be obtained with this procedure.

With some polymeric systems, polymeric particles prepared using a single or double emulsion technique vary in size depending on the size of the droplets. If droplets in water-in-oil emulsions are not of a suitably small size to form particles with the desired size range, smaller droplets can be prepared, for example, by sonication or homogenation of the emulsion, or by the addition of surfactants.

If the particles prepared by any of the above methods have a size range outside of the desired range, particles can be sized, for example, using a sieve, and further separated according to density using techniques known to those of skill in the art.

The polymeric particles are preferably prepared by spray drying. Prior methods of spray drying, such as that disclosed in PCT WO 96/09814 by Sutton and Johnson, disclose the preparation of smooth, spherical microparticles of a water-soluble material with at least 90% of the particles possessing a mean size between 1 and 10 μm. The method disclosed herein provides rough (non-smooth), non-spherical microparticles that include a water-soluble material combined with a water-insoluble material. At least 90% of the particles possess a mean size between 5 and 30 μm, and a low mass or tap density (less than 0.4 g/cc).

The particles can incorporate various complexes of therapeutic or diagnostic agents to be delivered with molecules of an opposite charge, or can include substances such as lipids which allow for the sustained release of small and large molecules. Addition of these complexes or substances is applicable to particles of any size and shape, and is especially useful for altering the rate of release of therapeutic agents from inhaled particles.

Aerodynamically Light Particles

Aerodynamically light particles, having a tap density less than about 0.4 g/cm$^3$ and an aerodynamic diameter between one and five microns, preferably between one and three microns, may be fabricated using the methods disclosed herein.

Aerodynamically Light Particle Size

The mass mean diameter of the particles can be measured using a Coulter Multisizer II (Coulter Electronics, Luton, Beds, England). The aerodynamically light particles in one preferred embodiment are at least about 5 microns in diameter. The diameter of particles in a sample will range depending upon factors such as particle composition and methods of synthesis. The distribution of size of particles in a sample can be selected to permit optimal deposition within targeted sites within the respiratory tract.

The aerodynamically light particles may be fabricated or separated, for example by filtration or centrifugation, to provide a particle sample with a preselected size distribution. For example, greater than 30%, 50%, 70%, or 80% of the particles in a sample can have a diameter within a selected range of at least 5 μm. The selected range within which a certain percentage of the particles must fall may be for example, between about 5 and 30 μm, or optionally between 5 and 15 μm. In one preferred embodiment, at least a portion of the particles have a diameter between about 9 and 11 μm. Optionally, the particle sample also can be fabricated wherein at least 90%, or optionally 95% or 99%, have a diameter within the selected range. The presence of the higher proportion of the aerodynamically light, larger diameter (at least about 5 μm) particles in the particle sample enhances the delivery of therapeutic or diagnostic agents incorporated therein to the deep lung.

In one embodiment, in the particle sample, the interquartile range may be 2 μm, with a mean diameter for example, between about 7.5 and 13.5 μm. Thus, for example, between at least 30% and 40% of the particles may have diameters within the selected range. Preferably, the said percentages of particles have diameters within a 1 μm range, for example, between 6.0 and 7.0 μm, 10.0 and 11.0 μm or 13.0 and 14.0 μm.

The aerodynamically light particles, optionally incorporating a therapeutic or diagnostic agent, with a tap density less than about 0.4 g/cm$^3$, mean diameters of at least about 5 μm, and an aerodynamic diameter of between one and five microns, preferably between one and three microns, are more capable of escaping inertial and gravitational deposition in the oropharyngeal region, and are targeted to the airways or the deep lung. The use of larger particles (mean diameter at least about 5 μm) is advantageous since they are able to aerosolize more efficiently than smaller, denser aerosol particles such as those currently used for inhalation therapies.

In comparison to smaller, relatively denser particles, the larger (at least about 5 μm) aerodynamically light particles also can potentially more successfully avoid phagocytic engulfment by alveolar macrophages and clearance from the lungs, due to size exclusion of the particles from the phagocytes' cytosolic space. Phagocytosis of particles by alveolar macrophages diminishes precipitously as particle diameter increases beyond 3 μm. Kawaguchi, H. et al., *Biomaterials* 7: 61–66 (1986); Krenis, L. J. and Strauss, B., *Proc. Soc. Exp. Med.,* 107:748–750 (1961); and Rudt, S. and Muller, R. H., *J. Contr. Rel.,* 22: 263–272 (1992). For particles of statistically isotropic shape, such as spheres with rough surfaces, the particle envelope volume is approximately equivalent to the volume of cytosolic space required within a macrophage for complete particle phagocytosis.

Aerodynamically light particles thus are capable of a longer term release of an encapsulated agent in the lungs. Following inhalation, aerodynamically light biodegradable particles can deposit in the lungs (due to their relatively low tap density), and subsequently undergo slow degradation and drug release, without the majority of the particles being phagocytosed by alveolar macrophages. The drug can be delivered relatively slowly into the alveolar fluid, and at a controlled rate into the blood stream, minimizing possible toxic responses of exposed cells to an excessively high concentration of the drug. The aerodynamically light particles thus are highly suitable for inhalation therapies, particularly in controlled release applications.

The preferred mean diameter for aerodynamically light particles for inhalation therapy is at least about 5 μm, for example between about 5 and 30 μm. The particles may be fabricated with the appropriate material, surface roughness, diameter and tap density for localized delivery to selected regions of the respiratory tract such as the deep lung or upper airways. For example, higher density or larger particles may be used for upper airway delivery, or a mixture of different sized particles in a sample, provided with the same or different therapeutic agent may be administered to target different regions of the lung in one administration.

Density and Deposition of Aerodynamically Light Particles

As used herein, the phrase "aerodynamically light particles" refers to particles having a tap density less than about 0.4 g/cm$^3$. The tap density of particles of a dry powder may be obtained using a GeoPyc™ (Micrometrics Instrument Corp., Norcross, Ga. 30093). Tap density is a standard measure of the envelope mass density. The envelope mass density of an isotropic particle is defined as the mass of the particle divided by the minimum sphere envelope volume within which it can be enclosed. Features which can contribute to low tap density include irregular surface texture and porous structure.

Inertial impaction and gravitational settling of aerosols are predominant deposition mechanisms in the airways and acini of the lungs during normal breathing conditions. Edwards, D. A., *J. Aerosol Sci.,* 26: 293–317 (1995). The importance of both deposition mechanisms increases in proportion to the mass of aerosols and not to particle (or envelope) volume. Since the site of aerosol deposition in the lungs is determined by the mass of the aerosol (at least for particles of mean aerodynamic diameter greater than approximately 1 μm), diminishing the tap density by increasing particle surface irregularities and particle porosity permits the delivery of larger particle envelope volumes into the lungs, all other physical parameters being equal.

The low tap density particles have a small aerodynamic diameter in comparison to the actual envelope sphere diameter. The aerodynamic diameter, $d_{aer}$, is related to the envelope sphere diameter, d (Gonda, I., "Physico-chemical principles in aerosol delivery," in *Topics in Pharmaceutical Sciences* 1991 (eds. D. J. A. Crommelin and K. K. Midha), pp. 95–117, Stuttgart: Medpharm Scientific Publishers, 1992)), by the formula:

$$d_{aer}=\sqrt{\rho}$$

where the envelope mass ρ is in units of g/cm$^3$. Maximal deposition of monodisperse aerosol particles in the alveolar region of the human lung (~60%) occurs for an aerodynamic diameter of approximately $d_{aer}=3$ μm. Heyder, J. et al., *J. Aerosol Sci.,* 17: 811–825 (1986). Due to their small envelope mass density, the actual diameter d of aerodynamically light particles comprising a monodisperse inhaled powder that will exhibit maximum deep-lung deposition is:

$$d=3/\sqrt{\rho}\,\mu m \text{ (where } \rho<1 \text{ g/cm}^3\text{);}$$

where d is always greater than 3 μm. For example, aerodynamically light particles that display an envelope mass density, ρ=0.1 g/cm$^3$, will exhibit a maximum deposition for particles having envelope diameters as large as 9.5 μm. The increased particle size diminishes interparticle adhesion forces. Visser, J., *Powder Technology,* 58:1–10. Thus, large particle size increases efficiency of aerosolization to the deep lung for particles of low envelope mass density, in addition to contributing to lower phagocytic losses.

Targeting of Particles

Targeting molecules can be attached to the particles via reactive functional groups on the particles. For example, targeting molecules can be attached to the amino acid groups of functionalized polyester graft copolymer particles, such as poly(lactic acid-co-lysine) (PLAL-Lys) particles. Targeting molecules permit binding interaction of the particle with specific receptor sites, such as those within the lungs. The particles can be targeted by attachment of ligands which specifically or non-specifically bind to particular targets. Exemplary targeting molecules include antibodies and fragments thereof including the variable regions, lectins, and hormones or other organic molecules capable of specific binding, for example, to receptors on the surfaces of the target cells.

Therapeutic Agents

Any of a variety of therapeutic or prophylactic agents can be incorporated within the particles, or used to prepare particles consisting solely of the agent and surfactant. The particles can be used to locally or systemically deliver a variety of incorporated agents to an animal. Examples include synthetic inorganic and organic compounds, proteins and peptides, polysaccharides and other sugars, lipids, and DNA and RNA nucleic acid sequences having therapeutic, prophylactic or diagnostic activities. Nucleic acid sequences include genes, antisense molecules which bind to complementary DNA to inhibit transcription, and ribozymes. The agents to be incorporated can have a variety of biological activities, such as vasoactive agents, neuroactive agents, hormones, anticoagulants, immunomodulating agents, cytotoxic agents, prophylactic agents, antibiotics, antivirals, antisense, antigens, and antibodies. In some instances, the proteins may be antibodies or antigens which otherwise would have to be administered by injection to elicit an appropriate response. Compounds with a wide range of molecular weight can be encapsulated, for example, between 100 and 500,000 grams or more per mole.

Proteins are defined as consisting of 100 amino acid residues or more; peptides are less than 100 amino acid residues. Unless otherwise stated, the term protein refers to both proteins and peptides. Examples include insulin and other hormones. Polysaccharides, such as heparin, can also be administered.

The polymeric aerosols are useful as carriers for a variety of inhalation therapies. They can be used to encapsulate small and large drugs, release encapsulated drugs over time periods ranging from hours to months, and withstand extreme conditions during aerosolization or following deposition in the lungs that might otherwise harm the encapsulated therapeutic.

The particles may include a therapeutic agent for local delivery within the lung, such as agents for the treatment of asthma, emphysema, or cystic fibrosis, or for systemic treatment. For example, genes for the treatment of diseases such as cystic fibrosis can be administered, as can beta agonists for asthma. Other specific therapeutic agents include, but are not limited to, insulin, calcitonin, leuprolide (or gonadotropin-releasing hormone ("LHRH")), granulocyte colony-stimulating factor ("G-CSF"), parathyroid hormone-related peptide, somatostatin, testosterone, progesterone, estradiol, nicotine, fentanyl, norethisterone, clonidine, scopolomine, salicylate, cromolyn sodium, salmeterol, formeterol, albuterol, and valium.

Those therapeutic agents which are charged, such as most of the proteins, including insulin, can be administered as a complex between the charged therapeutic agent and a molecule of opposite charge. Preferably, the molecule of opposite charge is a charged lipid or an oppositely charged protein.

Diagnostic agents

Any of a variety of diagnostic agents can be incorporated within the particles, which can locally or systemically deliver the incorporated agents following administration to a patient. Any biocompatible or pharmacologically acceptable gas can be incorporated into the particles or trapped in the pores of the particles using technology known to those skilled in the art. The term gas refers to any compound which is a gas or capable of forming a gas at the temperature at which imaging is being performed. In one embodiment, retention of gas in the particles is improved by forming a gas-impermeable barrier around the particles. Such barriers are well known to those of skill in the art.

Other imaging agents which may be utilized include commercially available agents used in positron emission tomography (PET), computer assisted tomography (CAT), single photon emission computerized tomography, x-ray, fluoroscopy, and magnetic resonance imaging (MRI).

Examples of suitable materials for use as contrast agents in MRI include the gadolinium chelates currently available, such as diethylene triamine pentacetic acid (DTPA) and gadopentotate dimeglumine, as well as iron, magnesium, manganese, copper and chromium.

Examples of materials useful for CAT and x-rays include iodine based materials for intravenous administration, such as ionic monomers typified by diatrizoate and iothalamate, non-ionic monomers such as iopamidol, isohexol, and ioversol, non-ionic dimers, such as iotrol and iodixanol, and ionic dimers, for example, ioxagalte.

Porous particles can be prepared which can be delivered via pulmonary delivery, and used, for example, for local or systemic delivery of incorporated agents and/or for imaging purposes. Particles incorporating diagnostic agents can be detected using standard techniques available in the art and commercially available equipment.

Administration

The particles may be administered alone or in any appropriate pharmaceutically acceptable carrier, such as a liquid, for example saline, or a powder, for administration to the respiratory system. They can be co-delivered with larger carrier particles, not including a therapeutic agent, the latter possessing mass mean diameters for example in the range between 50 μm and 100 μm.

Aerosol dosage, formulations and delivery systems may be selected for a particular therapeutic application, as described, for example, in Gonda, I. "Aerosols for delivery of therapeutic and diagnostic agents to the respiratory tract," in *Critical Reviews in Therapeutic Drug Carrier Systems,* 6:273–313, 1990; and in Moren, "Aerosol dosage forms and formulations," in: *Aerosols in Medicine. Principles, Diagnosis and Therapy,* Moren, et al., Eds, Esevier, Amsterdam, 1985.

The greater efficiency of aerosolization by the particles disclosed herein relative to particles that do not include a surfactant or a charged complex of a therapeutic agent permits more of a therapeutic agent to be delivered. The use of biodegradable polymers permits controlled release in the lungs and long-time local action or systemic bioavailability. Denaturation of macromolecular drugs can be minimized during aerosolization since macromolecules can be contained and protected within a polymeric shell. Coencapsulation of peptides with peptidase-inhibitors can minimize peptide enzymatic degradation. Pulmonary delivery advantageously can eliminate the need for injection. For example, the requirement for daily insulin injections can be avoided.

The present invention will be further understood by reference to the following non-limiting examples.

EXAMPLE 1

Synthesis of Aerodynamically Light Poly[(p-carboxyphenoxy)-hexane anhydride] ("PCPH") Particles Aerodynamically light poly[(p-carboxyphenoxy)-hexane anhydride] ("PCPH") particles were synthesized as follows. 100 mg PCPH (MW~25,000) was dissolved in 3.0 mL methylene chloride. To this clear solution was added 5.0 mL 1% w/v aqueous polyvinyl alcohol (PVA, MW~25,000, 88 mole % hydrolyzed) saturated with methylene chloride, and the mixture was vortexed (Vortex Genie 2, Fisher Scientific) at maximum speed for one minute. The resulting milky-white emulsion was poured into a beaker containing 95 mL 1% PVA and homogenized (Silverson Homogenizers) at 6000 RPM for one minute using a 0.75 inch tip. After homogenization, the mixture was stirred with a magnetic stirring bar and the methylene chloride quickly extracted from the polymer particles by adding 2 mL isopropyl alcohol. The mixture was continued to stir for 35 minutes to allow complete hardening of the microparticles. The hardened particles were collected by centrifugation and washed several times with double distilled water. The particles were freeze dried to obtain a free-flowing powder void of clumps. Yield, 85–90%.

The mean diameter of a typical batch prepared by this protocol is 6.0 μm, however, particles with mean diameters ranging from a few hundred nanometers to several millimeters may be made with only slight modifications. Scanning electron micrograph photos of a typical batch of PCPH particles showed the particles to be highly porous with irregular surface shape. The particles have a tap density less than 0.4 $g/cm^3$.

A surfactant such as DPPC may be incorporated into the polymer solution prior to particle formation, or optionally the particles can be ionically or covalently coated by surfactant on the particle surface after particle formation, or the surfactant may be absorbed onto the particle surface.

EXAMPLE 2

Synthesis of Spray-Dried Particles

Aerodynamically Light Particles Containing Polymer and Drug Soluble in Common Solvent Aerodynamically light 50:50 PLGA particles were prepared by spray drying with testosterone encapsulated within the particles according to the following procedures. 2.0 g poly (D,L-lactic-co-glycolic acid) with a molar ratio of 50:50 (PLGA 50:50, Resomer RG503, B.I. Chemicals, Montvale, N.J.) and 0.50 g testosterone (Sigma Chemical Co., St. Louis, Mo.) are completely dissolved in 100 mL dichloromethane at room temperature. The mixture is subsequently spray-dried through a 0.5 mm nozzle at a flow rate of 5 mL/min using a Buchi laboratory spray-drier (model 190, Buchi, Germany). The flow rate of compressed air is 700 nl. The inlet temperature is set to 30° C. and the outlet temperature to 25° C. The aspirator is set to achieve a vacuum of −20 to −25 bar. The yield is 51% and the mean particle size is approximately 5 μm. Larger particle size can be achieved by lowering the inlet compressed air flow rate, as well as by changing other variables. The particles are aerodynamically light, as determined by a tap density less than or equal to 0.4 $g/cm^3$ and an aerodynamic diameter between one and five microns. Porosity and surface roughness can be increased by varying the inlet and outlet temperatures, among other factors.

Aerodynamically Light Particles Containing Polymer and Drug in Different Solvents Aerodynamically light PLA particles with a model hydrophilic drug (dextran) were prepared by spray drying using the following procedure. 2.0 mL of an aqueous 10% w/v FITC-dextran (MW 70,000, Sigma Chemical Co.) solution was emulsified into 100 mL of a 2% w/v solution of poly (D,L-lactic acid) (PLA, Resomer R206, B.I. Chemicals) in dichloromethane by probe sonication (Sonics & Materials, Model VC-250 sonicator, Danbury, Conn.). The emulsion is subsequently spray-dried at a flow rate of 5 mL/min with an air flow rate of 700 nl/h (inlet temperature=30° C., outlet temperature=21 ° C., −20 mbar vacuum). The yield is 56%.

Aerodynamically Light Protein Particles

Aerodynamically light lysozyme particles were prepared by spray drying using the following procedure. 4.75 g lysozyme (Sigma) was dissolved in 95 mL double distilled water (5% w/v solution) and spray-dried using a 0.5 mm nozzle and a Buchi laboratory spray-drier. The flow rate of compressed air was 725 nl/h. The flow rate of the lysozyme solution was set such that, at a set inlet temperature of between 97 and 100° C., the outlet temperature is between 55 and 57° C. The aspirator was set to achieve a vacuum of −30 mbar. The enzymatic activity of lysozyme was found to be unaffected by this process and the yield of the aerodynamically light particles was 66%.

Aerodynamically Light High-Molecular Weight Water-Soluble Particles

Aerodynamically light dextran particles were prepared by spray drying using the following procedure. 6.04 g DEAE dextran (Sigma) was dissolved in 242 mL double distilled water (2.5% w/v solution) and spray-dried using a 0.5 mm nozzle and a Buchi laboratory spray-drier. The flow rate of compressed air was 750 nl/h. The flow rate of the DEAE-dextran solution was set such that, at a set inlet temperature of 155° C., the outlet temperature was 80° C. The aspirator was set to achieve a vacuum of −20 mbar. The yield of the aerodynamically light particles was 66%.

Aerodynamically Light Low-Molecular Weight Water-Soluble Particles

Aerodynamically light trehalose particles were prepared by spray drying using the following procedure. 4.9 g trehalose (Sigma) was dissolved in 192 mL double distilled water (2.5% w/v solution) and spray-dried using a 0.5 mm nozzle and a Buchi laboratory spray-drier. The flow rate of compressed air 650 nl/h. The flow rate of the trehalose solution was set such that, at a set inlet temperature of 100° C., the outlet temperature was 60° C. The aspirator was set to achieve a vacuum of −30 mbar. The yield of the aerodynamically light particles was 36%.

Aerodynamically Light Low-Molecular Weight Water-Soluble Particles

Polyethylene glycol (PEG) is a water-soluble macromolecule, however, it cannot be spray dried from an aqueous solution since it melts at room temperatures below that needed to evaporate water. As a result, PEG was spray-dried at low temperatures from a solution in dichloromethane, a low-boiling organic solvent. Aerodynamically light PEG particles were prepared by spray drying using the following procedure. 5.0 g PEG (MW between 15,000 and 20,000, Sigma) was dissolved in 100 mL double distilled water (5.0% w/v solution) and spray-dried using a 0.5 mm nozzle and a Buchi laboratory spray-drier. The flow rate of compressed air 750 nl/h. The flow rate of the PEG solution was set such that, at a set inlet temperature of 45° C., the outlet temperature was between 34 and 35° C. The aspirator was set to achieve a vacuum of −22 mbar. The yield of the aerodynamically light particles (tap density less than 0.4 g/cm$^3$) was 67%.

A surfactant such as DPPC may be incorporated into the polymer solution prior to particle formation, or optionally the particles can be ionically or covalently coated by surfactant on the particle surface after particle formation, or the surfactant may be absorbed onto the particle surface.

Materials and Methods

The following materials and methods were used in Examples 3 and 4.

Materials

The polymers: poly(D,L-lactic-co-glycolic acid) (PLGA) with a molar ratio of 50:50 and reported molecular weights of 100,000 Daltons (PLGA RG506) and 34,000 Daltons (PLGA RG503), and poly(D,L-lactic acid) with a reported molecular weight of 100,000 Daltons (PLA R206) were obtained from Boehringer Ingelheim (distributed by B.I. Chemicals, Montvale, N.J.). Fluorescently labelled FITC-Dextran with an average molecular weight of 19,000, and L,α-phosphatidylcholine dipalmitoyl (DPPC) were purchased from Sigma Chemical Company, St. Louis, Mo.

Microsphere Preparation: Double Emulsion

A double-emulsion solvent-evaporation procedure (Cohen, S., et al., *Pharm. Res.*, 8(6): 713–720 (1991); and Tabata, Y., et al., *Pharm. Res.*, 10(4): 487–496 (1993)), was modified to prepare microspheres for aerosolization. Briefly, 300 µl of an aqueous FITC-Dextran solution (50 mg/ml) was emulsified on ice into a 4.0 ml polymer solution in methylene chloride (200 mg polymer) by sonication at output 3 (Model VC-250, Sonics & Materials Inc., Danbury, Conn.) using a microtip for 5–10 s to form the inner-emulsion. The first emulsion was poured into 100 ml 1.0% aqueous PVA solution and homogenized (Model LD4 Homogenizer, Silverson Machines Ltd, England) at 6000 RPM using a ⅝" tip for 1 min to form the double emulsion. The microspheres were continuously stirred for 3 hours to allow hardening, collected by centrifugation, washed several times with double-distilled water, and freeze-dried into a freely flowing powder. Microspheres containing DPPC were prepared by dissolving DPPC in the polymer solution at a concentration of 3 mg/ml prior to the initial emulsification.

Microsphere Preparation: Spray Drying

The model hydrophilic drug, dextran labeled with fluorescein isothiocynate (FITC-Dextran), was encapsulated into PLA or PLGA by a novel emulsion/spray method. For example, 2.0 ml of an aqueous 10% w/v FITC-Dextran (MW=70,000, Sigma Chemical Co.) solution was emulsified into 100 ml of a 2% w/v solution of PLA in dichloromethane by probe sonication. The emulsion was subsequently spray-dried using a Büchi Mini Spray Drier (Model 190, Büchi Instruments, Germany) at a flow rate of 5 ml/min with an inlet air flow rate of 700 nl/h, inlet temperature of 30° C., outlet temperature of 21° C., and vacuum of −20 mbar. When DPPC was incorporated it was dissolved in the polymer solution at a concentration of 2 mg/ml prior to emulsification and spray drying.

Microsphere Size Distribution Analysis

Microsphere size distributions were determined using a Coulter Multisizer II (Coulter Electronics Limited, Luton, Beds, England). Approximately 10 drops Coulter type IA non-ionic dispersant were added, followed by 2 mL isoton II solution (Coulter), to 5–10 mg microspheres, and the spheres were dispersed by brief vortex mixing. This suspension was added to 50 mL isoton II solution until the coincidence of particles was between 5 and 8%. Greater than 500,000 particles were counted for each batch of spheres.

Drug Distribution by Confocal Microscopy

For confocal microscopy, a few milligrams of microspheres containing FITC-Dextran as the drug were suspended in glycerin by brief probe sonication (Vibra-cell Model VC-250 Sonicator, ⅛" microtip probe, Sonics & Materials Inc., Danbury, Conn.) at output 4 (50W). A drop of the suspension was placed onto a glass slide and a glass cover slip was applied and held in place with finger nail polish. The suspension was allowed to settle for one hour before being viewed by confocal microscopy (Bio-Rad MRC-600 Confocal, Axioplan microscope).

Microsphere Morphology by Scanning Electron Microscopy (SEM)

Microsphere morphology was observed by scanning electron microscopy (SEM) using a Stereoscan 250 MK3 microscope from Cambridge Instruments (Cambridge, Mass.) at 15 kV. Microspheres were freeze-dried, mounted on metal stubs with double-sided tape, and coated with gold prior to observation.

Microsphere Density Analysis

Microsphere bulk density was estimated by tap density measurements and confirmed by mercury intrusion analysis at Porous Materials, Inc. (Ithaca, N.Y.).

Determination of Amount FITC-Dextran and DPPC Encapsulated

The amount of model drug, FITC-Dextran, encapsulated into microspheres was determined by dissolving 10.0 mg microspheres in 3.0 ml 0.8 N NaOH overnight at 37° C., filtering with a 0.45 μm filter (Millipore), and measuring the fluorescence relative to a standard curve (494 nm excitation and 525 mn emission) using a fluorimeter. The drug loading was determined by dividing the amount of FITC-Dextran encapsulated by the theoretical amount if it all were encapsulated. The amount of surfactant, DPPC, encapsulated into microspheres was determined by dissolving 10.0 mg of microspheres in chloroform and using the Stewart Assay (New, R.R.C., "Characterization of Liposomes," in *Liposomes: A Practical Approach,* R. New, Editor, IRL Press, New York, 105–161 (1990)).

In Vitro Aerosolization and Inertial Deposition Behavior

The in vitro microparticle aerodynamic characteristics were studied using an Andersen Mark I Cascade Impactor (Andersen Samplers, Atlanta, Ga.) at an air flow rate of 28.3 l/min. The metal impaction plates were coated with a thin film of Tween 80 minimize particle bouncing Turner, J. and S. Hering, *J. Aerosol Sci.,* 18: 215–224 (1987). Gelatin capsules (Eli Lilly) were charged with 20 mg of microparticles and loaded into a Spinhaler® inhalation device (Fisons, Bedford, Mass.). The aerosolization experiments were done in triplicate. In each experiment, 10 inhalers were discharged for 30 seconds into the impactor. A 60-second interval was observed between every two consecutive aerosolizations. Fractions of microspheres deposited on each of nine stages, corresponding to stages 0 to 7, and the filter (F) of the impactor, were collected in volumetric flasks by carefully washing the plates with NaOH solution (0.8 N) in order to provide degradation of the polymer and complete dissolution of the fluorescent material. After 12 hours of incubation at 37° C., the solutions were filtered with a 0.45 μm filter and the amount of fluorescent material in each stage was measured at 494 nm (excitation) and 525 nm (emission) using a fluorimeter. Respirable fraction of the delivered dose was calculated according to the fluorescence measurements as percentages of the total fluorescence (i.e., that amount collected in stages 0 to Filter) compared with that collected in stages 2 to Filter of the Impactor.

In Vivo Particle Distribution Following Aerosolization in Rats

Male Sprague Dawley rats (between 150 and 200 g) were anesthetized using a mixture of ketamine (90 mg/kg) and xylazine (10 mg/kg). The anesthetized rat was placed ventral side up on a surgical table provided with a temperature controlled pad to maintain physiological temperature. The animal was cannulated above the carina with an endotracheal tube connected to a Harvard ventilator (Rodent Ventilator Model 683, South Natick, Mass.). The animal was force ventilated for 20 minutes at 300 ml/min. 50 mg of microspheres made with or without DPPC were introduced into the endotracheal tube. Following the period of forced ventilation, the animal was sacrificed and the lungs and trachea were separately washed using broncholalveolar lavage as follows: a tracheal cannula was inserted, tied into place, and the airways were washed with 10 ml aliquots of phenol red-free Hanks balanced salt solution (Gibco, Grand Island, N.Y.) without $Ca^{2+}$ and $Mg^{2+}$ (HBSS). The lavage procedure was repeated until a total volume of 30 ml was collected. The lavage fluid was centrifuged (400 g) and the pellets collected and resuspended in 2 ml HBSS. 100 μl was removed for particle counting using a hemacytometer. The remaining solution was mixed with 10 ml of 0.4 N NaOH. After incubation at 37° C. for 12 hours, the fluorescence of each solution was measured (wavelengths of 494 nm excitation, 525 nm emission) using a fluorimeter.

EXAMPLE 3

Fabrication of PLGA microspheres by a Double Emulsion Process Which Encapsulate a Model High-Molecular-Weight Drug, FITC-Dextran Scanning electron microscopy "SEM" photographs showing surface morphology of microspheres (MS) made by the double emulsion process with and without the lung surfactant, DPPC were obtained. By SEM, the microspheres made with and without DPPC by the double emulsion process had very similar surface characteristics and size distribution, as confirmed by size distribution measurements, shown below in Table 1.

The efficient entrapment of DPPC within microspheres (83% of theoretical ±11% standard deviation, n=6) was confirmed by dissolving an aliquot of MS in chloroform and detecting the DPPC concentration in solution by the Stewart Assay, as shown in Table 1. Particles made by double emulsion with DPPC are easily resuspended in aqueous solution after lyophilization and are lump-free when dry as determined by light microscopy. Particles made by the double emulsion process without DPPC resuspend easily, however, they appear somewhat agglomerated when dry by light microscopy.

TABLE 1

Characteristics of Microparticles used for In Vitro and In Vivo Aerosolization[a]

| Sample | Mass-Mean (True) Diameter, (μm) | DPPC Load (μg/mg spheres) | DPPC Loading Efficiency, (%) | FITC-Dextran (Model Drug) Loading Efficiency, (%) |
|---|---|---|---|---|
| MS without DPPC | 8.5 ± 0.76 | 0 | N/A | 95.8 |
| MS with DPPC | 8.2 ± 0.18 | 45 ± 6 | 83 ± 11 | 82.4 |

[1]Values are given ± standard deviation.

Confocal microscopy was used to evaluate the distribution of the model drug, FITC-Dextran ($M_w$ 19,000), throughout microspheres made without DPPC and with DPPC. In each case, the drug is evenly dispersed throughout the polymer matrix, which can lead to prolonged delivery of macromolecules after placement in an aqueous environment.

The density of the microspheres as determined by mercury intrusion analysis is shown in Table 2 (and confirmed by tap density measurements).

TABLE 2

| Comparison of Porous Microparticles with Bulk (PLGA 50:50) Polymer | | |
|---|---|---|
| Sample | Density, $\rho_{MS}$ (g/cc) | Respirable Size Range, $d_{resp}$ ($\mu$m) |
| Bulk PLGA | 1.35 | 0.69–4.05 |
| MS without DPPC | 0.37 ± 0.03 | 1.3–7.7 |
| MS with DPPC | 0.30 ± 0.06 | 1.46–8.58 |

Using the concept of aerodynamic diameter (Gonda, I., in *Topics in Pharmaceutical Sciences* 1991, D. Crommelin and K. Midha, Editors, Stuttgart: Medpharm Scientific Publishers, pp. 95–117 (1992)), it is possible to determine the size range of the microspheres which are theoretically respirable given their mass density, $\rho_{MS}$. Specifically, it can be shown below in Equation 2 that:

$$\frac{0.8}{\sqrt{\rho_{MS}}} \leq d_{resp} \leq \frac{4.7}{\sqrt{\rho_{MS}}} \quad (2)$$

where $d_{resp}$ corresponds to the diameter of particles (in $\mu$m) theoretically able to enter and remain in the airways without inertial or gravitational deposition (particles smaller than this range are exhaled), and where $\rho_{MS}$ is in units of g/cc. The theoretical respirable size range of the microspheres also is shown in Table 2. The optimal size range (i.e., $d_{resp}$) for a non-porous PLGA 50:50 microsphere is 0.69–4.05 $\mu$m (Table 2). The optimal respirable size range for microspheres without DPPC is 1.3–7.7 $\mu$m and, for microspheres with DPPC, 1.46–8.58 $\mu$m (Table 2). The upper limit on size of respirable particles is increased from 4.05 to greater than 8.5 $\mu$m when DPPC is used in the PLGA microsphere preparation. Therefore, the use of low density DPPC microspheres allows the use of larger particles for aerosolization, which may have advantages for drug delivery, such as less particle-particle interaction due to decreased surface area to volume ratio, and lower susceptibility to phagocytosis by alveolar macrophages. In addition, a primary effect of DPPC is to render the particles less adhesive and therefore allow improved aerosolization, as demonstrated below.

Figure 2:
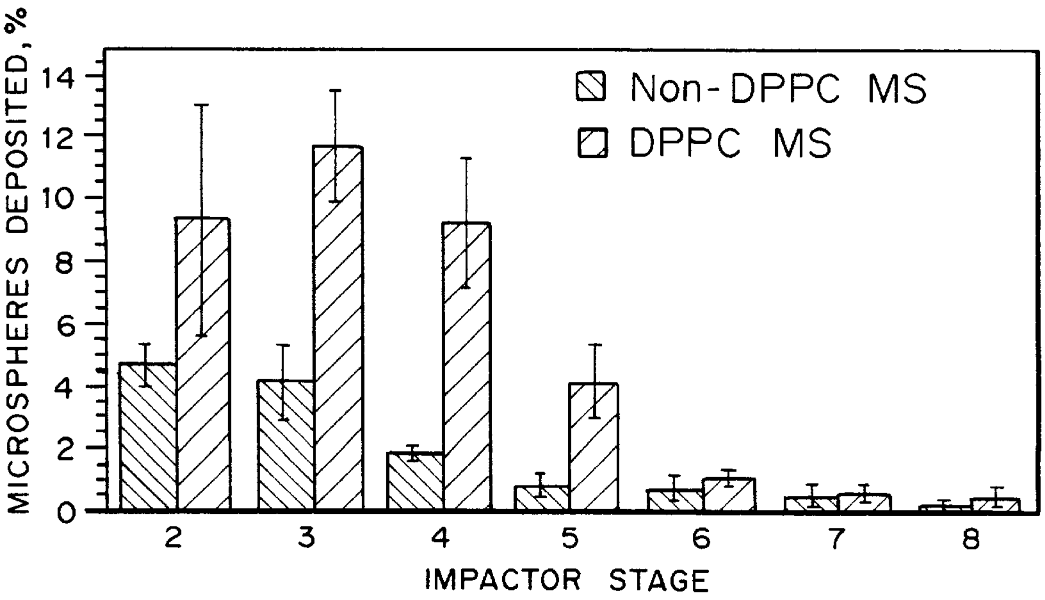
FIG. 2 is a graph comparing the mass fraction of the aerosolized dose that is deposited in different stages of a cascade impactor after in vitro aerosolization of PLGA microspheres made by a double emulsion procedure with and without the incorporation of DPPC.

FIGS. 1 and 2 show the results of an in vitro aerosolization of the PLGA microspheres made by a double emulsion process with and without DPPC. The microspheres were aerosolized as a dry powder released from a Spinhaler® dry powder inhaler (DPI). FIG. 1 illustrates the mass-fraction of the initial dose that is released from the dry powder inhaler device (DPI Efficiency) using an Andersen Mark I Cascade Impactor. DPI efficiencies approaching 80% were obtained with microspheres made with and without DPPC. Although the DPI efficiencies for the two batches were nearly the same, a great difference can be seen between microspheres made with and without DPPC when their deposition within the cascade impactor is observed (FIG. 2).

FIG. 2 shows the mass fraction of aerosolized particles that is deposited in stages 2 through Filter (2-Filter) of the Andersen cascade impactor, considered the stages corresponding to the respirable fraction of the microspheres. Stages 0 and 1 correspond roughly to the mouth and throat, and to the upper airways of the lung, respectively. Stages 2-F correspond to successively deeper fractions of the lung. It can be seen that a much greater percentage of microspheres make it to the latter stages of the impactor (considered deeper portions of the lungs) when DPPC is used in their preparation. Overall, greater than 35% (37.0±2.1) of aerosolized particles made with DPPC are considered respirable compared with 13.2±2.9% without DPPC, as shown in Table 3. The large difference in respirable fraction between the DPPC and non-DPPC particles is at least in part attributed to reduced particle-particle interaction due to the use of DPPC.

In order to estimate the theoretical respirable fraction (RF) of the microspheres, and compare it with experimentally measured in vitro and in vivo RF's, size distribution measurements were analyzed to determine the percentage of particles (by mass) of each type (DPPC and non-DPPC) that were within the theoretical respirable size range (i.e., $d_{resp}$ Table 2). As shown in Table 3, a higher percentage of particles made with DPPC are expected to be respirable compared with non-DPPC particles (63 to 51%, respectively). This theoretical respirable fraction is based on the mass fraction of microspheres with diameters in the respirable size range, $d_{resp}$ as defined by Eq. (2), and therefore takes into account the different sizes and densities of the two batches of microspheres.

TABLE 3

| Comparison of Microparticle Aerosolization Properties In Vitro | | |
|---|---|---|
| Sample | Theoretical Respirable Fraction (i.e., Mass % of microspheres in Respirable Size Range)[a] | Measured Respirable Fraction (%, In Vitro[b]) |
| microspheres without DPPC | 51 ± 6 | 13.2 ± 2.9 |
| microspheres with DPPC | 63 ± 2 | 37.0 ± 2.1 |

[a]Based on theoretical respirable size range ($d_{resp}$ Table 2) and size distribution analyses.
[b]Measured using an Andersen Mark I Cascade Impactor.

To determine whether agglomeration forces during particle aerosolization from the Spinhaler device might be playing a role even after the particles enter the impactor system (i.e., primarily non-DPPC particles remain agglomerated in the inspired stream, resulting in deposition in the first two impactor stages: stages 0 and 1), in vivo aerosolization experiments were performed in which particles were permitted to fall by gravity into the inspiration stream of a Harvard ventilator system joined with the trachea of an anesthetized rat. In this model, approximately 63% of the inhaled DPPC-PLGA particles deposit in the airways and distal lung regions, whereas 57% of the non-DPPC particles are able to penetrate beyond the trachea in the lungs. These respirable fractions are much nearer to the predicted respirable fractions based upon particle diameter and mass density (Table 3).

Particle aggregation thus is less with DPPC-containing PLGA particles than without DPPC, even though the particles are of similar size and surface morphological features. The use of DPPC thus appears to reduce interparticle attractions, such as van der Waals and electrostatic attractions. It is also possible that the presence of DPPC reduces moisture absorption which may cause particle-particle interaction by capillary forces.

In addition to the biocompatibility features of DPPC and improvement of surface properties of microspheres for aerosolization, it is possible that the release of DPPC from the slow-eroding PLGA microspheres in the alveolar region of the lungs can more effectively insure the maintenance of normal surfactant fluid composition thereby minimizing the possibility of local toxic side effects. The alveolar surfactant fluid layer is, on average, 10 nm thick (Weibel, E. R., *Morphometry of the Human Lung,* New York: Academic Press (1963).

EXAMPLE 4

Fabrication of PLGA Microspheres by Spray Drying which Encapsulate a Model High Molecular Weight Drug, FITC-Dextran Microspheres were made by spray drying using a variety of polymeric carriers with and without the incorporation of DPPC. The results are summarized in Table 4.

TABLE 4

Characterization of Spray Dried Microparticulates

| Sample | Mass-Mean (True) Diameter, (μm) | DPPC Load (μg/mg spheres) and Efficiency (%) | FITC-Dextran Loading Efficiency, (%) | % of Surface Coated with DPPC by ESCA |
|---|---|---|---|---|
| R206 + DPPC | 5.4 | [a] | 54.9 | [a] |
| R206 − DPPC | 4.4 | — | 64.8 | — |
| RG503 + DPPC | 2.0 | 62.8 | 65.2 | 46.5% |
| RG503 − DPPC | 3.0 | — | 78.2 | — |
| RG506 + DPPC | 4.3 | 89.1 | 62.7 | 42–62% |
| RG506 − DPPC | [b] | — | 100 | — |

[a]Not Determined
[b]No reliable determination because the powder was highly aggregated.

Figure 3:
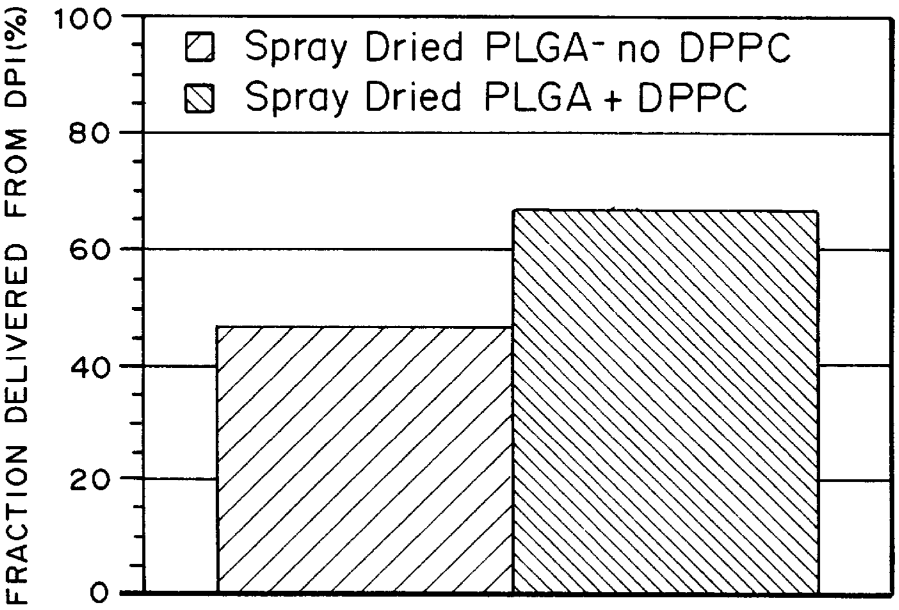
FIG. 3 is a graph showing the aerosolization behavior of PLGA microspheres made by spray drying with and without the incorporation of DPPC showing the mass-fraction of the initial dose that is released from the dry powder inhaler device after in vitro aerosolization.
Figure 4:
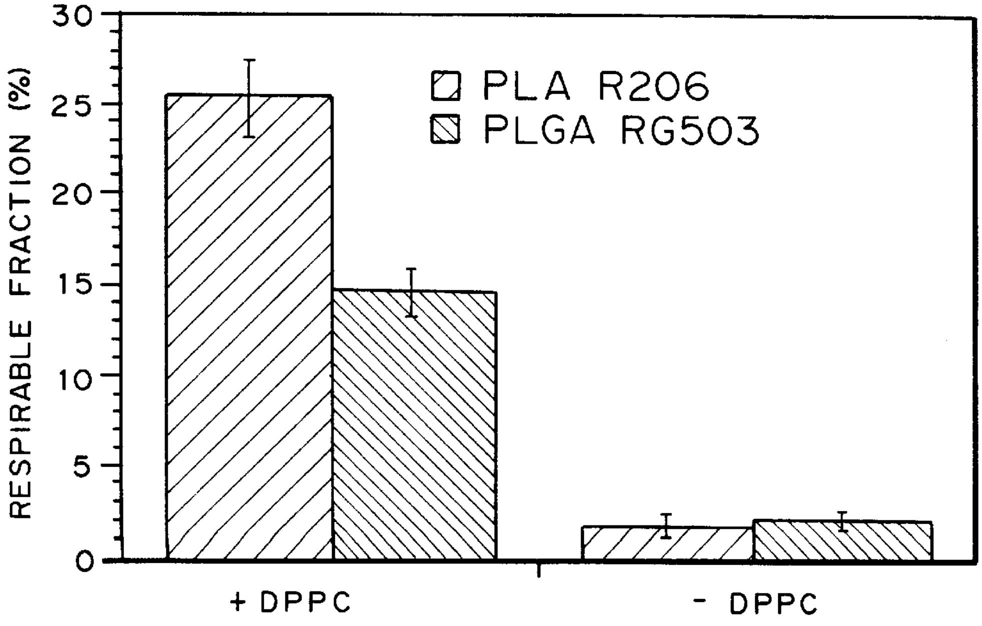
FIG. 4 is a graph comparing the in vitro aerosolization behaviors of PLA and PLGA microspheres made by spray drying with and without the incorporation of DPPC showing the mass-fraction of the aerosolized dose that is deposited in stages of a cascade impactor corresponding to the "respirable-fraction".

Aerosolization properties of the microspheres also were examined, as shown in Table 5. Microspheres made by spray drying with and without DPPC have similar size distributions (Table 5) and mass densities (0.49±0.04 g/cc). However, the aerosolization performance of spray-dried aerosols made with and without DPPC is markedly different. FIG. 3 shows that the fraction of low-molecular-weight PLGA RG503 microparticles that are aerosolized from the dry powder inhaler (i.e., the % of particles that leave the DPI upon simulated inhalation, defined as the DPI Efficiency) is 70.4% when the particles are made with DPPC compared with only 46.8% for particles made without DPPC. Furthermore, the deposition of all types of polymer microparticles following aerosolization into an Andersen impactor is greatly improved using DPPC-coated particles (Table 5). Without the use of DPPC, ≦2% of the particles aerosolized reach the latter stages of the impactor (those corresponding to the respirable fraction, stages 2-Filter). On the other hand, a maximum of 25.6% of DPPC-coated microspheres reach stages 2-Filter, as shown in FIG. 4. Higher respirable fractions may be obtained with particles that contain low molecular weight drugs that are soluble in methylene chloride and therefore do not require the use of water during their preparation.

TABLE 5

Summary of Aerosolization Data of microspheres Prepared by Spray Drying with or without DPPC

| Sample | % Aerosolized Particles that reach stages 1 - Filter | % Aerosolized Particles that reach stages 2 - Filter | % Aerosolized Particles that reach stages 3 - Filter | DPI Efficiency |
|---|---|---|---|---|
| R206 + DPPC | 40.4 ± 8.4 | 25.6 ± 2.3 | 18.0 ± 2.7 | 38.6 ± 3.7 |
| R206 − DPPC | 7.4 ± 2.1 | 1.8 ± 0.5 | 1.1 ± 0.3 | 41.0 ± 4.8 |
| RG503 + DPPC | 36.0 ± 9.2 | 14.7 ± 1.53 | 10.4 ± 0.46 | 70.4 ± 2.4 |
| RG503 − DPPC | 3.3 ± 0.6 | 2.1 ± 0.3 | 2.0 ± 0.3 | 46.8 ± 8.0 |
| RG506 + DPPC | 13.7 ± 9.1 | 7.1 ± 4.1 | 4.1 ± 2.5 | 76.6 ± 8.4 |
| RG506 − DPPC | 1.8 ± 0.6 | 1.6 ± 0.6 | 1.4 ± 0.7 | 74.0 ± 7.2 |

R206 = PLA, molecular weight approximately 100,000.
RG503 = PLGA 50:50, molecular weight approximately 34,000.
RG506 = PLGA 50:50, molecular weight approximately 100,000.

EXAMPLE 5

Fabrication of Estradiol-Containing Lactose:DPPC Particles

Materials and Methods: A Niro Atomizer Portable Spray Dryer (Model #68) was used for all of the following Examples. Compressed air with variable pressure ran a rotary atomizer located above the dryer. Liquid feed with varying rate was pumped continuously by an electronic metering pump (LMI, model #A151-192s) to the atomizer. Both inlet and outlet temperatures can be measured and controlled manually. A container was tightly attached to the cyclone to collect the spray dried powder product.

Estradiol-containing particles were prepared to illustrate the preparation of large porous particles that contain a relatively large drug fraction by weight. Estradiol particles of standard mass density (greater than 0.4 g/cc) can be made in various ways. In this example, the particles included 30% β-estradiol, 62% lactose and 8% DPPC by weight. The lactose was dissolved in deionized water and the estradiol and DPPC were dissolved in 95% v/v ethanol. The two solutions were combined to form an 85% v/v ethanol solution. The total concentration of powdered starting materials in the solution was 3.25% w/v. The solution was spray dried under the following condition: The inlet temperature was 160° C.; the outlet temperature was 95° C.; the atomization pressure was 2 kp/cm$^2$ (28.45 psi); and the feed rate was 34 ml/min. The resulting spray dried powder had a tap (mass) density of 0.46 g/ml. The mean diameter based on volume, as measured using a Microtrac particle sizer, was 3.5 μm, thus giving an aerodynamic diameter of 2.4 μm.

In another example, estradiol particles of standard mass density (about 1 g/cc) were prepared by spray drying a solution containing 70% estradiol and 30% DPPC with a total powder concentration of 1.9% w/v in 85% v/v ethanol. The spray dryer was operated under the following conditions; the inlet temperature was 150° C., the outlet temperature was 85° C., the atomization pressure was 1 kp/cm$^2$ (14.22 psi), and the feed rate was 30 ml/min. The particles produced had a tap density of 0.62 g/ml and a mean diameter of 6 μm, thus giving an approximate aerodynamic diameter of 4.7 μm.

In order to produce light, porous particles, many combinations of operating conditions and powder compositions were tested. Another example of the preparation of low density particles was as follows; A solution of 90% β-estradiol and 10% DPPC by weight in 95% ethanol was prepared. The solution was then combined with deionized water to make a solution of 85% ethanol. The total powder concentration was 1.1% w/v. The operating conditions were as follows; the inlet temperature was 110° C., the outlet temperature was 85° C., the atomization pressure was 1 kp/cm$^2$ (14.22 psi), and the feed rate was 30 ml/min. The yield was 53.0%. The resulting powder was very flowable, and was made up of particles possessing irregular shapes and rough surfaces, as viewed by a SEM (scanning electron microscope). The mean diameter, determined by the Microtrac, based on volume was 6 μm. The tap density was 0.28, thus giving an approximate aerodynamic diameter of 2.6 microns, which falls within the desired range of between one and five microns.

EXAMPLE 6

Preparation of Lactose:DPPC Carrier Particles

"Carrier" particles can be created to mimic drug-carrying particles with similar excipient concentrations. Case studies of four carrier particles are discussed below, followed by two examples of adding small concentrations of drug to the carrier particle. In this example, a small weight percentage of drug in the particle is considered to be less than 20% of the total powder weight.

Carrier particles with standard mass density can be prepared via several methods. An example is the following formulation. Solution of lactose in deionized water and DPPC in ethanol were combined to provide a solution containing relative ratios of 67% lactose and 33% DPPC by weight in 85% ethanol, with the total powder concentration in the solution of about 0.1% w/v. The solution was spray dried under the following conditions; the inlet temperature was 200° C.; the outlet temperature was 119° C.; the atomization pressure was 3 kp/cm$^2$ (42.72 psi); and the feed rate was 40 ml/min. The yield of this run was 29.3%. The resulting spray dried powder had a tap (mass) density of 0.41 g/ml and a mean diameter by volume average estimated from an SEM of 2.5 μm, thus giving an approximated aerodynamic diameter of 1.6 microns, which is within the desired range of between one and five microns.

Powder composition, powder concentration, solvent composition and spray drier operating conditions are some of the factors which can be varied in order to produce light, porous carrier particles. Large, porous particles can be made that have a donut-like morphology. Such particles can be prepared, for example, by preparing a solution that includes 33% human albumin, 33% lactose, and 33% DPPC by weight. The human albumin and lactose was dissolved in deionized water and the DPPC was dissolved in 95% ethanol. The two solutions were combined to yield an 85% ethanol solution. The total powder concentration was about 0.1% w/v. The solution was spray dried under the following conditions; the inlet temperature was 110° C.; the outlet temperature was 60° C.; the atomization pressure was 3 kp/cm$^2$ (42.72 psi); and the feed rate was 40 ml/min. The yield from this run was 38.5%. The tap (mass) density of the resulting particles was 0.16 g/ml, and the size of this particle on the coulter counter is 7.6 μm, thus giving an approximate aerodynamic diameter of 3.0 μm. (Note: The volume average sizes approximated from the SEM and those determined by the Coulter Counter can be considered equivalent.)

EXAMPLE 7

Preparation of Albumin:Lactose:DPPC Particles.

Another type of large, porous particles looks similar to a dried grape. Particles with this type of morphology can be prepared, for example, by spray drying a solution that contains 20% human albumin, 20% lactose, and 60% DPPC by weight. The human albumin and lactose were dissolved in deionized water and the DPPC was dissolved in 95% ethanol. The two solutions were combined to form an 85% ethanol solution. The total powder concentration was about 0.1% w/v. The solution was spray dried under the following conditions; the inlet temperature was 110° C.; the outlet temperature was 60° C.; the atomization pressure was 3 kp/cm$^2$ (42.72 psi); and the feed rate was 40 ml/min. The yield was 45.0%. The tap (mass) density of this particle is 0.05 g/ml, and the approximate volume-average size of this particle from the SEM was 7 μm, thus giving an approximate aerodynamic diameter of 1.6 μm. Aerosilization studies of this particle yielded the following results; aerosolized fraction was 58.5%; respirable fraction was 26.6%, and respirable fraction of inhaled aerosol was 43.8%.

EXAMPLE 8

Preparation of Albumin:Lactose:DPPC Particles

Various methods can be used to increase the size of the particles. The particles prepared in this example had roughly the same morphology as those in Example 7, but had a larger particle size. The particles were prepared as follows: A solution of 20% human albumin, 20% lactose, and 60% DPPC by weight was spray dried. The human albumin and lactose were dissolved in deionized water and the DPPC was dissolved in 95% ethanol. The two solutions were combined to form an 85% ethanol solution. The total powder concentration was about 0.2% w/v. The solution was spray dried under the following conditions; the inlet temperature was 110° C.; the outlet temperature was 51° C.; the atomization pressure was 2 kp/cm$^2$ (28.48 psi); and the feed rate was 66 ml/min. The yield from this run was 48.6%. The tap (mass) density of the resulting particles was 0.04 g/ml, and the approximate volume-average size of the particles from the SEM was 10 μm, thus giving an approximate aerodynamic diameter of 2.0 microns.

EXAMPLE 9

Spray Drying of Insulin:Albumin:Lactose:DPPC Particles

This example demonstrates that adding less than 20% drug by weight has little change on the particle morphology, size, tap density, and aerosolization characterizations. For example, human insulin was added at a concentration of about 2% by weight of the particles in Example 7. The particles were prepared by spray drying a solution of 2% human insulin, 19% human albumin, 19% lactose, and 60% DPPC by weight. The human insulin, human albumin and lactose were dissolved in deionized water and the DPPC was dissolved in 95% ethanol. The solubility of human insulin in the deionized water was increased by adding a few drops of NaOH (5g NaOH/100 ml deionized water) until the insulin went into solution. The two solutions were combined to form an 85% ethanol solution. The total powder concentration was about 0.1% w/v. The solution was spray dried under the following conditions; the inlet temperature was 110° C.; the outlet temperature of 61° C.; the atomization pressure was 3 kp/cm$^2$ (42.72 psi); and the feed rate was 40 ml/min. The yield from this run was 51.1%. The tap (mass) density of the resulting particles was 0.05 g/ml and the approximate volume-average size of this particle from the SEM was 6.5 μm, thus giving an approximate aerodynamic diameter of 1.5 μm. The morphology of the particles was very similar to the particles in Example 7. Aerosolization studies of these particles yielded the following results: the aerosolized fraction was 45.0%; the respirable fraction was 15.0%; the respirable fraction of the inhaled aerosol was 58.3%.

EXAMPLE 10

Preparation of Albuterol Particles

Albuterol particles with a relatively small amount of drug by weight were also prepared. In this example, particles were prepared according to the procedure in Example 6, except that 4% albuterol by weight of the particle was added. The particles were formed by spray drying a solution containing 4% albuterol, 33% human albumin, 33% lactose, and 33% DPPC by weight. The albuterol, human albumin and lactose were dissolved in deionized water and the DPPC was dissolved in 95% ethanol. The solutions were combined to form an 85% ethanol solution. The total powder concentration was about 0.1% w/v. The solution was spray dried under the following conditions; the inlet temperature was 110° C.; the outlet temperature was 60° C.; the atomization pressure was 3 kp/$cm^2$ (42.72 psi); and the feed rate was 40 ml/min. The yield from this run was 46.8%. The tap (mass) density of the resulting particles was 0.15 g/ml and the size of the particles as measured on a Coulter counter was 7.2 μm, thus giving an approximate aerodynamic diameter of 2.8 μm.

EXAMPLE 11

Preparation of Sustained Release Insulin Particles

Sustained release of insulin out of the particles was achieved by rendering the insulin insoluble. Insulin was dissolved in ultrapure water (0.02% w/v). Protamine was then added (in the proportion insulin/protamine 5/1 w/w) to form an insulin/protamine complex. The formation of the insulin/protamine complex causes the insulin to precipitate. The complex was dissolved by raising the pH to about 5 with HCl so that the solution could be spray dried. Lactose was then added to the solution. The aqueous solution was then mixed with a 95% v/v ethanol solution containing DPPC. The final concentration of each excipient in the 85% v/v solution was insulin/protamine/lactose/DPPC 210.4/37.6/60% w/v. The solution was spray dried under the following conditions; the inlet temperature was 110° C.; the outlet temperature was 60° C.; the atomization pressure was 3 kp/$cm^2$ (42.72 psi); and the feed rate was 40 ml/min. The ability of the particles to provide sustained release in vitro was evaluated. Particles suspended in phosphate buffer saline at pH 7.4 released less than 10% of the incorporated insulin after 5 hours.

EXAMPLE 12

Preparation of Insulin:Protamine:Zinc Complexes

Particles containing a complex of insulin/protamine/zinc were prepared according to the process in Example 11. The concentration of each excipient in the ethanol/water (85:15% v/v) solution was insulin/protamine/zinc chloride/lactose/DPPC 2:0.6:0.25:32.4:60 (% w/v). The solution was spray dried under the same conditions in Example 11. The formulation was also shown to provide sustained release of insulin in vitro.

Figure 5:
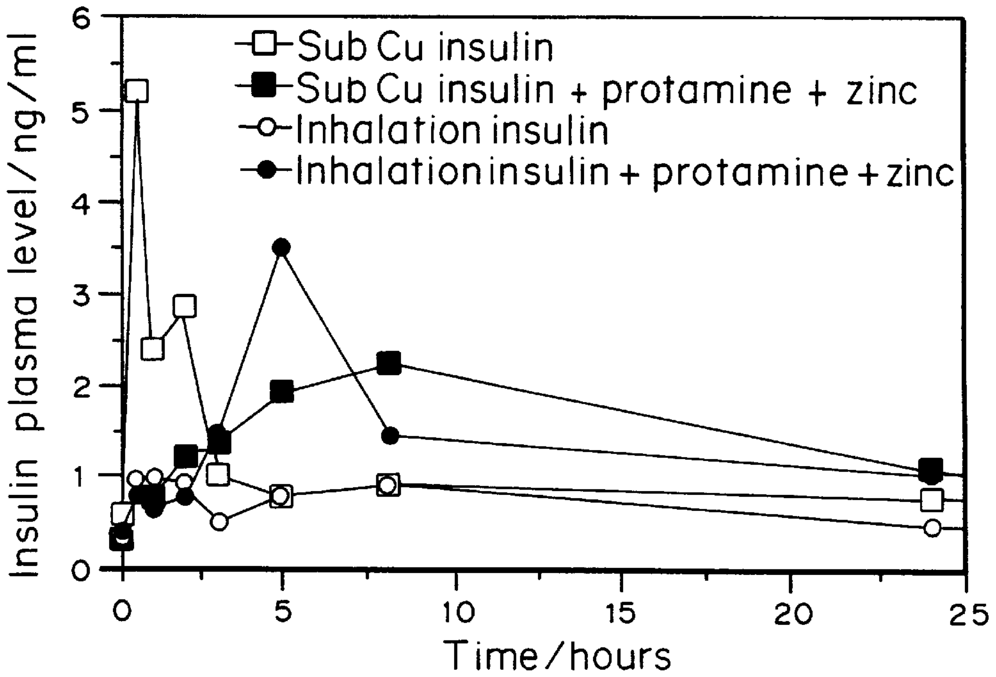
FIG. 5 is a graph comparing the plasma concentration of insulin (ng/ml) per unit time (hrs).

The particles (8 mg) were inhaled into the lungs of rats using the procedures described in Edwards, et al. (*Science,* 276, 1868 (1997)). For comparison purposes, the particles were also injected subcutaneously and non-sustained insulin particles of identical insulin content (without protamine or zinc) were injected subcutaneously and inhaled. FIG. 5 shows the plasma concentration per unit time for insulin administered via the various modes of administration. The inhaled protamine/zinc particles resulted in sustained high serum insulin concentrations for at least 24 hours, in contrast to particles without protamine or zinc, which released insulin in less than approximately 5 hours.

Therapeutics other than insulin can be complexed in the same manner and included in the particles. Proteins having an isoelectric point (pI) lower than the physiological pH of 7.4 as insulin (pI=5.3) can be precipitated in the same manner using protamine (e.g., growth hormone, pI=4.9). Proteins having a pI higher than pH of 7.4 (e.g., LHRH, calcitonin) can be precipitated using a negatively charged compound (e.g., dextran-sulfate) or by adding an appropriate salt. This approach can be extended to drugs (e.g., heparin) other than therapeutic proteins as well.

EXAMPLE 13

Preparation of Sustained Release Albuterol Particles

Figure 6:
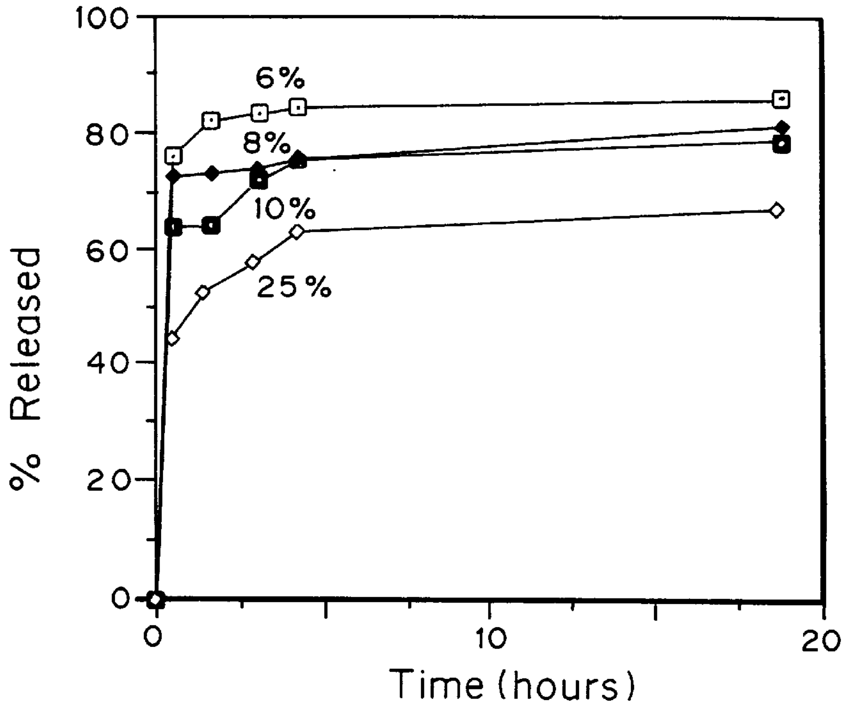
FIG. 6 is a graph comparing the release of albuterol (%) over time (hrs).

Albuterol particles were prepared to evaluate the sustained release of a hydrophilic molecule from particles. The albuterol-containing particles were prepared as described in Example 7, reducing the percentages of lactose and albumin (while keeping the ratio equal) and adding cholesterol (of varying percentages; 6, 8, 10, 25%) and albuterol (4%). The addition of cholesterol led to an increasingly slower release of albuterol, as shown in FIG. 6. Albuterol concentration was measured using a UV spectrophotometer. The data shown in FIG. 6 demonstrates that cholesterol can be incorporated into particles to provide sustained albuterol release. Similar results can be achieved by increasing the DPPC concentration beyond 60%.

EXAMPLE 14

Release Properties of Albumin:DPPC:Lactose:Albuterol Particles

Figure 7:
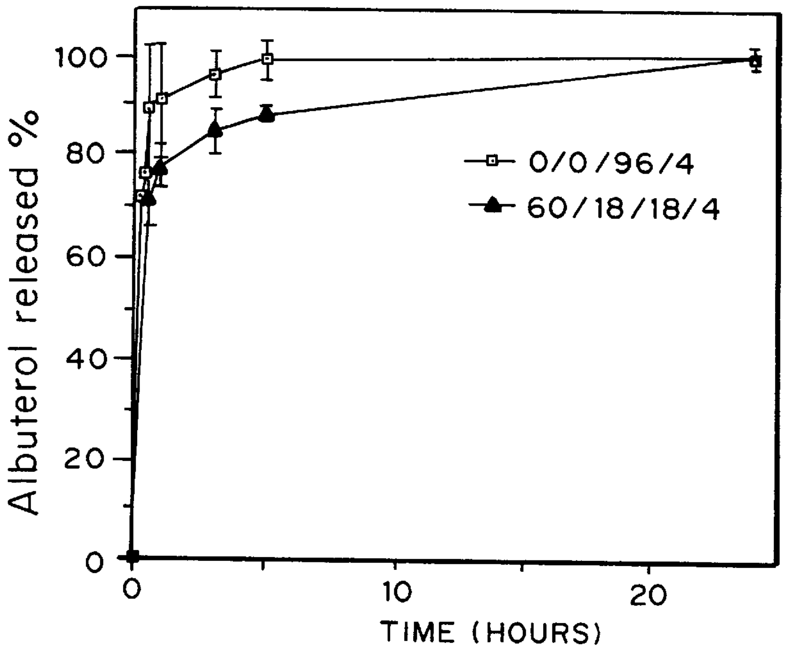
FIG. 7 is a graph comparing the in vitro release of albuterol (%) over time (hrs) for compositions with varying ratios of DPPC, albumin, lactose and albuterol.

Particles (mean diameter 10 μm, tap density 0.06 $gram^3$) were prepared particles as described in Example 7 with 60% DPPC, 18% albumin, 18% lactose, and 4% albuterol to demonstrate that sustained release of a hydrophilic molecule such as albuterol can also be achieved without cholesterol. The in vitro release of albuterol is shown in FIG. 7 both for this formulation and a non-sustained release formulation that included only lactose (96%) and albuterol (4%). Even without cholesterol, the release of the albuterol was sustained for nearly 24 hours.

Figure 8:
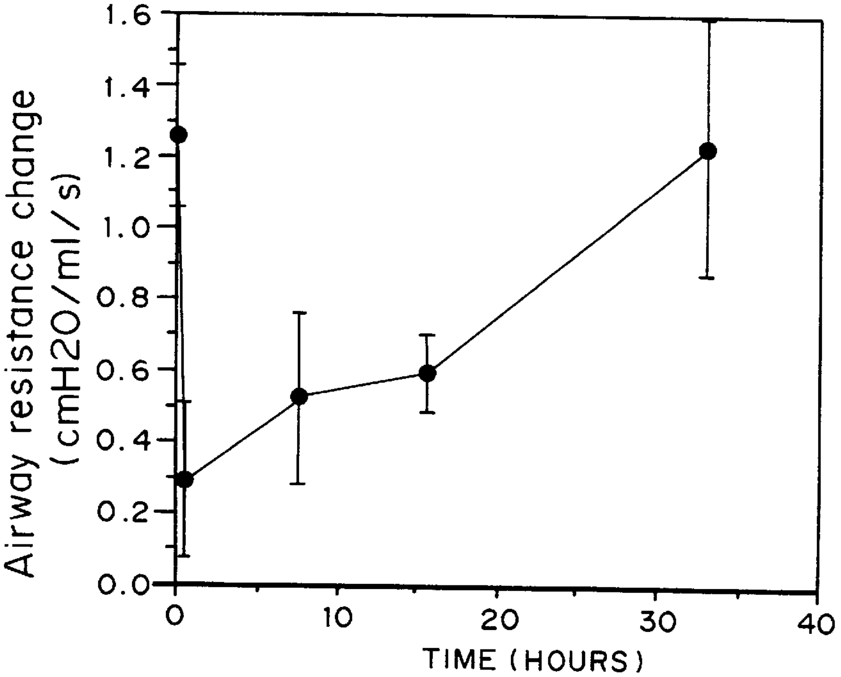
FIG. 8 is a graph comparing the airway resistance change (cm $H_2O$/ml/sec.) per unit time (hrs).

Particles (5 mg, i.e. 200 μg albuterol dose) were administered to guinea pigs using the procedures in Example 12 to demonstrate that the sustained release albuterol particles could produce sustained bronchodilation. The animals were administered carbachol prior to measuring airway resistance. Airway resistance was monitored using a Buxco system. Airway resistance dropped sharply following inhalation of the large porous particles (FIGS. 7 and 8) and remained at statistically low levels for approximately 1 day (n=y).

"Placebo" particles (60% DPPC, 20% albumin, 20% lactose) prepared as described in Example 11 were also administered. Airway resistance following carbachol challenge was measured at eight hours following inhalation and 15 hours following inhalation. The airway resistance was 1.0±0.3 and 1.0±0.2 cm $H_2O$/ml/sec., proving that the bronchodilation observed in FIG. 8 was due to slow albuterol release.

Slow albuterol release has also been achieved in vitro using particles prepared by the methods of Example 7 with 10% DPPC, 86% albumin, and 4% albuterol. However particles prepared with 10% DPPC, 43% albumin, 43% lactose, and 4% albuterol did not display significantly slower albuterol release in vitro, indicating that for relatively low DPPC content, high albumin content is favorable for sustained albuterol release.

These examples demonstrate that by choosing the composition of the spray dried materials and by varying the spray drying parameters, the aerodynamic properties of the inhaled particles can be effectively controlled. More specifically, the composition of the spray dried material especially affects the density and shape of the particles while the spray drying parameters have a stronger affect on their size. For instance, increasing the proportion of lactose in the particles make the particles heavier, while increasing the albumin or dipalmitoyl phosphatidylcholine (DPPC) content makes them lighter. Increasing DPPC content also increases the particle size. Nevertheless, when a relatively small proportion of drug is incorporated in the particles, the characteristics of the particles remain relatively unaffected. Decreasing the inlet temperature largely increases the size of the particles without greatly affecting their tap density. Increasing the feed rate and decreasing the pressure of the compressed air both tend to increase the size of the particles without greatly affecting their density. However, these effects are smaller than those of the temperature.

We claim:

1. Particles for drug delivery to the pulmonary system consisting of a therapeutic agent and a material selected from the group consisting of surfactant and a molecule having a charge opposite to the charge of the therapeutic agent and forming a complex thereto, wherein the particles have a tap density less than 0.4 g/cm$^3$ and a mean diameter between 5 $\mu$m and 30 $\mu$m effective to yield an aerodynamic diameter of the particles of between approximately one and five microns.

2. The composition of claim 1 wherein the aerodynamic diameter of the particles is between approximately one and three microns.

3. The composition of claim 1 wherein at least 50% of the particles have a mean diameter between 5 $\mu$m and 15 $\mu$m and a tap density less than 0.1 g/cm$^3$.

4. The composition of claim 1 further comprising a pharmaceutically acceptable carrier for administration to the lungs.

5. The composition of claim 1 wherein the particles comprise a complex of charged molecules and a surfactant.

6. The composition of claim 1 wherein the therapeutic agent is selected from the group consisting of proteins, polysaccharides, lipids, nucleic acids and combinations thereof.

7. The composition of claim 1 wherein the therapeutic agent is selected from the group consisting of nucleotides and oligonucleotides.

8. The composition of claim 6 wherein the therapeutic agent is selected from the group consisting of insulin, calcitonin, leuprolide and albuterol.

9. The composition of claim 1 wherein the surfactant is selected from the group consisting of a fatty acid, a phospholipid, and a block copolymer.

10. The composition of claim 9 wherein the surfactant is a phosphoglyceride.

11. The composition of claim 9 wherein the surfactant is L-α-phosphatidylcholine dipalmitoyl.

12. The composition of claim 1 wherein the agent is a charged species and is present as a complex with an oppositely charged species.

13. The composition of claim 12 wherein the agent is hydrophilic and is present as a complex with a hydrophobic moiety.

14. A method for drug delivery to the pulmonary system comprising:

administering to the respiratory tract of a patient in need of treatment an effective amount of particles consisting of a therapeutic agent and a molecule selected from the group consisting of surfactant and a molecule having a charge opposite to the charge of the therapeutic agent and forming a complex thereto, wherein the particles have a tap density less than about 0.4 g/cm$^3$ and a mean diameter of between 5 $\mu$m and 30 $\mu$m effective to yield an aerodynamic diameter of the particles of between approximately one and five microns.

15. The method of claim 14 wherein the aerodynamic diameter of the particles is between approximately one and three microns.

16. The method of claim 14 wherein at least 50% of the administered particles have a mean diameter between 5 $\mu$m and 15 $\mu$m.

17. The method of claim 14 wherein at least 50% of the administered particles have a mean diameter between 5 $\mu$m and 15 $\mu$m and a tap density of less than about 0.1 g/cm$^3$.

18. The method of claim 14 wherein the particles comprise a complex of charged molecules and surfactant.

19. The method of claim 14 for delivery to the alveolar zone of the lung wherein at least 90% of the particles have a mean diameter between about 9 $\mu$m and 11 $\mu$m and a tap density less than 0.1 g/cm$^3$.

20. The method of claim 14 wherein the therapeutic agent is selected from the group consisting of proteins, polysaccharides, lipids, nucleic acids and combinations thereof.

21. The method of claim 14 wherein the therapeutic agent selected from the group consisting of nucleotides and oligonucleotides.

22. The method of claim 20 wherein the therapeutic agent is selected from the group consisting of insulin, calcitonin, leuprolide and albuterol.

23. The method of claim 14 wherein the surfactant is selected from the group consisting of a fatty acid, a phospholipid, and a block copolymer.

24. The method of claim 23 wherein the surfactant is a phosphoglyceride.

25. The method of claim 23 wherein the surfactant is L-α-phosphatidylcholine dipalmitoyl.

26. The method of claim 14 wherein the agent is a charged species and is present as a complex with an oppositely charged species.

27. The method of claim 14 wherein the agent is hydrophilic and is present as a complex with a hydrophobic moiety.

* * * * *

UNITED STATES PATENT AND TRADEMARK OFFICE

CERTIFICATE OF CORRECTION

PATENT NO. : 5,985,309

DATED : November 16, 1999

INVENTOR(S) : David A. Edwards, Robert S. Langer, Rita Vanbever, Jeffrey Mintzes, Jue Wang and Donghao Chen It is certified that error appears in the above-identified patent and that said Letters Patent is hereby corrected as shown below:

On the title page of the patent under [73] Assignee: please insert the following:

The Penn State Research Foundation, University Park, Pennsylvania 16802

UNITED STATES PATENT AND TRADEMARK OFFICE
CERTIFICATE OF CORRECTION

PATENT NO. : 5,985,309

DATED : November 16, 1999

INVENTOR(S) : David A. Edwards, Robert S. Langer, Rita Vanbever, Jeffrey Mintzes, Jue Wang and Donghao Chen It is certified that error appears in the above-identified patent and that said Letters Patent is hereby corrected as shown below:

On the title page of the patent under [63] please delete:
"Continuation of application No. 08/784,421, Jan. 16, 1997" and insert therefor:
-- This application is a Continuation-in-Part of co-pending U.S. Application No. 08/739,308, filed October 29, 1996, now U.S. Patent No. 5,874,064, which is a Continuation-in-Part of U.S. Application No. 08/655,570, filed May 24, 1996. This application is a Continuation-in-Part of co-pending U.S. Application No. 09/194,068, filed May 23, 1997, which is a national stage application of PCT/US97/08895 filed May 23, 1997, which is a Continuation-in-Part of U.S. Application Nos. 08/655,570, filed May 24, 1996 and 08/739,308, filed October 29, 1996. This application is also a Continuation-in-Part of U.S. Application No. 08/784,421, filed January 16, 1997, now U.S. Patent No. 5,855,913. This application is also a Continuation-in-Part of U.S. Application No. 08/655,570, filed May 24, 1996.--

UNITED STATES PATENT AND TRADEMARK OFFICE

CERTIFICATE OF CORRECTION

PATENT NO. : 5,985,309
DATED : November 16, 1999
INVENTOR(S) : David A. Edwards, Robert S. Langer, Rita Vanbever, Jeffrey Mintzes, Jue Wang and Donghao Chen It is certified that error appears in the above-identified patent and that said Letters Patent is hereby corrected as shown below:

In Column 1, beginning at line 4 after the title delete:

"This application claims the benefit of U.S. Provisional application Ser. No. 60/059,004 filed Sep. 15, 1997, and a continuation of Ser. No. 08/784,421 filed Jan. 16. 1997"

and insert therefor:

–This Application is a Continuation-in-Part of co-pending U.S. Application No. 08/739,308, filed October 29, 1996, now U.S. Patent No. 5,874,064, which is a Continuation-in-Part of U.S. Application No. 08/655,570, filed May 24, 1996. This Application is a Continuation-in-Part of co-pending U.S. Application No. 09/194,068, filed May 23, 1997, which is a national stage application of PCT/US97/08895 filed May 23, 1997, which is a Continuation-in-Part of U.S. Application Nos. 08/655,570, filed May 24, 1996 and 08/739,308, filed October 29, 1996. This application is also a Continuation-in-Part of U.S. Application No. 08/784,421, filed January 16, 1997, now U.S. Patent No. 5,855,913, and claims the benefit of U.S. Provisional Application No. 60/059,004, filed September 15, 1997. This Application is also a Continuation-in-Part of U.S. Application No. 08/655,570 filed May 24, 1996. All of the above identified applications are incorporated herein by reference.--

UNITED STATES PATENT AND TRADEMARK OFFICE

CERTIFICATE OF CORRECTION

PATENT NO. : 5,985,309

DATED : November 16, 1999

INVENTOR(S) : David A. Edwards, Robert S. Langer, Rita Vanbever, Jeffrey Mintzes, Jue Wang, Donghao Chen It is certified that error appears in the above-identified patent and that said Letters Patent is hereby corrected as shown below:

-- This invention was made with government support under Grant Number HD29129 awarded by the National Institutes of Health. The government has certain rights in the invention. --

Signed and Sealed this

Twenty-seventh Day of February, 2001

Attest:

Nicholas P. Godici

NICHOLAS P. GODICI

Attesting Officer

*Acting Director of the United States Patent and Trademark Office*

UNITED STATES PATENT AND TRADEMARK OFFICE

CERTIFICATE OF CORRECTION

PATENT NO. : 5,985,309 C1
DATED : December 31, 2002
INVENTOR(S) : David A. Edwards et al.

It is certified that error appears in the above-identified patent and that said Letters Patent is hereby corrected as shown below:

Title page,
Item [73], Assignee, delete "The Penn State Research Foundation" and replace with -- Massachusetts Institute of Technology and The Penn State Research Foundation --.

Signed and Sealed this

Twenty-seventh Day of May, 2003

JAMES E. ROGAN
*Director of the United States Patent and Trademark Office*

UNITED STATES PATENT AND TRADEMARK OFFICE

CERTIFICATE OF CORRECTION

PATENT NO. : 5,985,309
APPLICATION NO. : 08/971791
DATED : November 16, 1999
INVENTOR(S) : David A. Edwards et al.

It is certified that error appears in the above-identified patent and that said Letters Patent is hereby corrected as shown below:

Under Column 1, after the Related Paragraph, line 7 replace with below:

--GOVERNMENT SUPPORT
This invention was made with government support under Grant Number HD029129, awarded by the National Institutes of Health. The government has certain rights in this invention--.

Signed and Sealed this
Thirtieth Day of August, 2011

David J. Kappos
*Director of the United States Patent and Trademark Office*

US005985309C1

(12) REEXAMINATION CERTIFICATE (4699th)

United States Patent

Edwards et al.

(10) Number: US 5,985,309 C1

(45) Certificate Issued: Dec. 31, 2002

(54) PREPARATION OF PARTICLES FOR INHALATION

(75) Inventors: David A. Edwards, State College, PA (US); Robert S. Langer, Newton, MA (US); Rita Vanbever, Cambridge, MA (US); Jeffrey Mintzes, State College, PA (US); Jue Wang, State College, PA (US); Donghao Chen, State College, PA (US)

(73) Assignee: The Penn State Research Foundation, University Park, PA (US)

Reexamination Request:
No. 90/006,093, Aug. 22, 2001

Reexamination Certificate for:
Patent No.: 5,985,309
Issued: Nov. 16, 1999
Appl. No.: 08/971,791
Filed: Nov. 17, 1997

Certificate of Correction issued Feb. 27, 2001.

Related U.S. Application Data

(63) Continuation of application No. 08/784,421, filed on Jan. 16, 1997, now Pat. No. 5,855,913.

(60) Provisional application No. 60/059,004, filed on Sep. 15, 1997.

(51) Int. Cl.$^7$ .................................................. A61K 9/12

(52) U.S. Cl. ............................ 424/46; 424/45; 424/43; 424/489; 424/491; 424/426; 424/434

(58) Field of Search ........................... 424/45, 46, 489, 424/491, 499, 426, 434

(56) References Cited

U.S. PATENT DOCUMENTS 5,458,135 A 10/1995 Patton et al. .......... 128/200.14
5,780,014 A 7/1998 Eljamal et al. ............... 424/46
5,795,594 A 8/1998 York et al. .................. 424/489
5,851,453 A 12/1998 Hanna et al. .................. 264/5
6,063,138 A 5/2000 Hanna et al. ................. 23/295

FOREIGN PATENT DOCUMENTS

WO WO 95/01221 1/1995
WO WO 95/01324 1/1995
WO WO 96/00610 1/1996

OTHER PUBLICATIONS

File History for U.S. patent application Ser. No. 08/423,515, filed Apr. 14, 1995, to Platz et al.

Gonda, I. "Physico–chemical principles in aerosol delivery," in *Topics of Pharmaceutical Sciences* 1991 (eds. D.J.A. Crommelin and K.K. Midha).

*Primary Examiner*—Jose' G. Dees

(57) ABSTRACT

Particles incorporating a surfactant and/or a hydrophilic or hydrophobic complex of a positively or negatively charged therapeutic agent and a charged molecule of opposite charge for drug delivery to the pulmonary system, and methods for their synthesis and administration are provided. In a preferred embodiment, the particles are made of a biodegradable material and have a tap density less than 0.4 g/cm$^3$ and a mass mean diameter between 5 $\mu$m and 30 $\mu$m, which together yield an aerodynamic diameter of the particles of between approximately one and three microns. The particles may be formed of biodegradable materials such as biodegradable polymers. For example, the particles may be formed of poly(lactic acid) or poly(glycolic acid) or copolymers thereof. Alternatively, the particles may be formed solely of a therapeutic or diagnostic agent and a surfactant. Surfactants can be incorporated on the particle surface for example by coating the particle after particle formation, or by incorporating the surfactant in the material forming the particle prior to formation of the particle. Exemplary surfactants include phosphoglycerides such as dipalmitoyl phosphatidylcholine (DPPC). The particles can be effectively aerosolized for administration to the respiratory tract to permit systemic or local delivery of wide a variety of therapeutic agents. Formation of complexes of positively or negatively charged therapeutic agents with molecules of opposite charge can allow control of the release rate of the agents into the blood stream following administration.

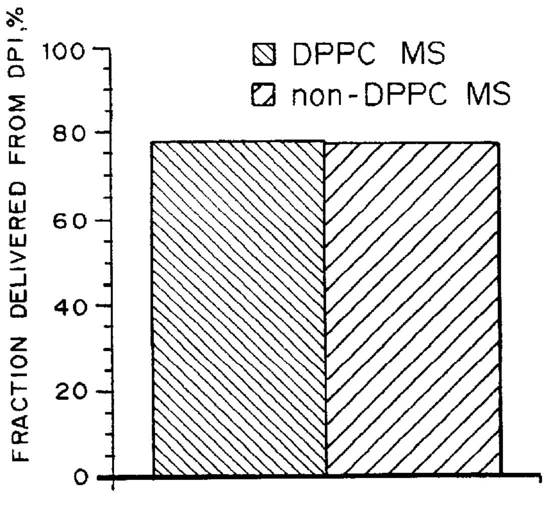

REEXAMINATION CERTIFICATE ISSUED UNDER 35 U.S.C. 307

NO AMENDMENTS HAVE BEEN MADE TO THE PATENT

AS A RESULT OF REEXAMINATION, IT HAS BEEN DETERMINED THAT:

The patentability of claims 1–27 is confirmed.

* * * * *